(12) United States Patent
Tout et al.

(10) Patent No.: US 10,232,155 B2
(45) Date of Patent: Mar. 19, 2019

(54) COMBINED SOLUTION PUMP AND STORAGE SYSTEM FOR USE WITH A REDUCED-PRESSURE TREATMENT SYSTEM

(71) Applicant: KCI Licensing, Inc., San Antonio, TX (US)

(72) Inventors: Aidan Marcus Tout, Alderbury (GB); Kenneth R. Smith, San Antonio, TX (US); Thomas Paul Lawhorn, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 1077 days.

(21) Appl. No.: 14/087,418

(22) Filed: Nov. 22, 2013

(65) Prior Publication Data

US 2014/0163487 A1    Jun. 12, 2014

Related U.S. Application Data

(60) Provisional application No. 61/729,926, filed on Nov. 26, 2012.

(51) Int. Cl.
*A61M 1/00* (2006.01)
*A61M 35/00* (2006.01)
*A61M 3/02* (2006.01)

(52) U.S. Cl.
CPC .......... *A61M 35/00* (2013.01); *A61M 1/0023* (2013.01); *A61M 3/0258* (2013.01);
(Continued)

(58) Field of Classification Search
CPC .. A61M 35/00; A61M 1/0023; A61M 3/0258; A61M 1/0084; A61M 1/0088;
(Continued)

(56) References Cited

U.S. PATENT DOCUMENTS 1,355,846 A    10/1920   Rannells
2,547,758 A    4/1951    Keeling
(Continued)

FOREIGN PATENT DOCUMENTS

AU    550575 A1    3/1986
AU    745271       4/1999
(Continued)

OTHER PUBLICATIONS

International Search Report and Written Opinion for corresponding PCT/US2013/071455 dated Feb. 28, 2014.
(Continued)

*Primary Examiner* — Tatyana Zalukaeva
*Assistant Examiner* — Andrew J Mensh

(57) ABSTRACT

A therapy device for instillation of fluid to a tissue site is described. The therapy device includes a base having a cartridge receptacle and a support coupled to the base to secure the base to a pole. The therapy device also includes a cartridge configured to engage the base when positioned in the cartridge receptacle. The therapy device also includes a pump head disposed within the cartridge receptacle and configured to engage the cartridge for movement of fluid. The cartridge includes a body forming at least a portion of a fluid reservoir and a tube segment coupled to the body and in fluid communication with the fluid reservoir. The tube segment is configured to engage the pump head.

17 Claims, 14 Drawing Sheets

(52) U.S. Cl.
 CPC ......... *A61M 1/0084* (2013.01); *A61M 1/0088* (2013.01); *A61M 3/0266* (2013.01); *A61M 2205/12* (2013.01); *A61M 2205/14* (2013.01); *A61M 2205/332* (2013.01); *A61M 2205/3375* (2013.01); *A61M 2205/502* (2013.01)

(58) Field of Classification Search
 CPC ............ A61M 3/0266; A61M 2205/12; A61M 2205/14; A61M 2205/332; A61M 2205/3375; A61M 2205/502
 USPC ........................................................ 604/319
 See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,604,089 A | 8/1986 | Santangelo et al. |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,024,720 A * | 2/2000 | Chandler ............ A61M 1/0058 604/35 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0032403 A1 * | 3/2002 | Savagle ............... A61M 1/0058 604/28 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0040700 A1 | 2/2003 | Hickle et al. |
| 2004/0202561 A1 * | 10/2004 | Hershberger .... A61B 17/32002 417/477.7 |
| 2006/0079852 A1 | 4/2006 | Bubb et al. |
| 2007/0078377 A1 * | 4/2007 | Mason ................ A61M 1/0058 604/27 |
| 2011/0004143 A1 | 1/2011 | Beiriger et al. |
| 2011/0190735 A1 * | 8/2011 | Locke ................ A61M 1/0058 604/543 |
| 2012/0289928 A1 * | 11/2012 | Wright ................ A61M 1/342 604/500 |

(56) References Cited

U.S. PATENT DOCUMENTS

| | | |
|---|---|---|
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2110564 A | 6/1983 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | 02/24253 A2 | 3/2002 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

(56) References Cited

OTHER PUBLICATIONS

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

English Summary of Notice of Rejection for corresponding Japanese Application No. 2015-544151 dated Aug. 1, 2017.

First Office Action for corresponding Chinese Application No. 201380062758.1, dated Feb. 28, 2017.

European Examination Report for corresponding Application 138083191, filed Apr. 4, 2018.

\* cited by examiner

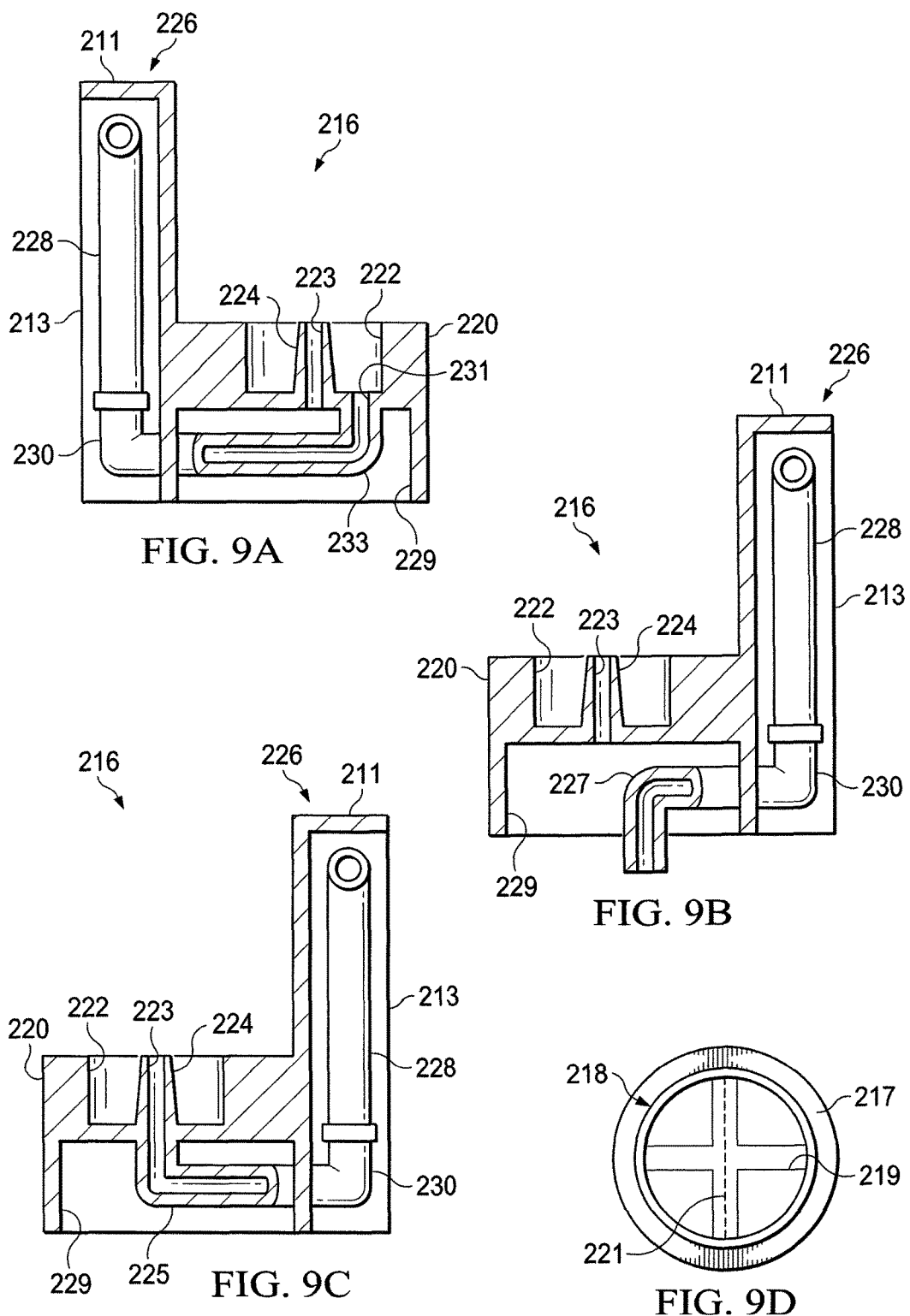

COMBINED SOLUTION PUMP AND STORAGE SYSTEM FOR USE WITH A REDUCED-PRESSURE TREATMENT SYSTEM

Under 35 U.S.C. § 119(e), this application claims priority to and the benefit of U.S. Provisional Patent Application No. 61/729,926 filed Nov. 26, 2012, entitled "Combined Solution Pump and Storage System for use with a Negative Pressure Treatment System," the disclosure of which is hereby incorporated by reference in its entirety.

TECHNICAL FIELD

The present disclosure relates generally to medical treatment systems for treating tissue sites that produce liquids, such as exudate, and for processing body fluids. More particularly, but not by way of limitation, the present disclosure relates to a system for volumetric delivery of solution with a therapy device.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure therapy," but is also known by other names, including "negative-pressure therapy," "negative-pressure wound therapy," "vacuum therapy," and "vacuum-assisted closure," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

In addition, the delivery of therapeutic fluids, such as saline or antibiotic fluids, to the tissue site can also provide healing benefits to the tissue site. Treatment of tissue sites with the delivery of therapeutic fluids may be referred to as "instillation therapy." Instillation therapy may assist in cleaning the tissue site by aiding in the removal of infectious agents or necrotic tissue. The therapeutic fluids used in instillation therapy may also include medicinal fluids, such as antibiotics, anti-fungals, antiseptics, analgesics, or other similar substances, to aid in the treatment of a tissue site.

While the clinical benefits of reduced-pressure therapy and instillation therapy are widely known, the cost and complexity of reduced-pressure therapy and instillation therapy can be a limiting factor in its application, and the development and operation of reduced-pressure systems, components, and processes continues to present significant challenges to manufacturers, healthcare providers, and patients.

SUMMARY OF ILLUSTRATIVE EMBODIMENTS

According to an illustrative embodiment, a therapy device for instillation of fluid to a tissue site is described. The therapy device may include a base having a cartridge receptacle and a support coupled to the base to secure the base to a pole. The therapy device may also include a cartridge configured to engage the base when positioned in the cartridge receptacle. The therapy device may further include a pump head disposed within the cartridge receptacle and configured to engage the cartridge for movement of fluid.

According to another illustrative embodiment, a solution cartridge for an instillation therapy device is described. The solution cartridge may include a body forming at least a portion of a fluid reservoir. A fill port fluidly may be coupled to the fluid reservoir and configured to receive fluid. A heat seal may be coupled to the fill port. The solution cartridge may include a tube segment coupled to the body and in fluid communication with the fluid reservoir. The tube segment may be configured to engage a pump head of a therapy device for movement of fluid from the fluid reservoir.

According to still another example embodiment, a solution cartridge for an instillation therapy device is described. The solution cartridge may include a body forming at least a portion of a fluid reservoir. The body may have an ovoid-shape with a rounded end and a flattened end opposite the rounded end. The body may include a fill port fluidly coupled to the fluid reservoir and configured to receive fluid and a cap coupled to the fill port. The solution cartridge may also include a tube segment coupled to the body and in fluid communication with the fluid reservoir. The tube segment may be configured to engage a pump head of a therapy device for movement of fluid from the fluid reservoir.

According to yet another embodiment, a solution cartridge for an instillation therapy device is described. The solution cartridge includes a carrier having a base housing and a tube housing. The solution cartridge also includes a fluid container having a port configured to engage the base housing. The solution cartridge may further include a tube segment disposed in the tube housing and coupled to the carrier. The tube segment may be configured to be in fluid communication with the fluid container and to engage a pump head of a therapy device for movement of fluid from the fluid container.

According to still another example embodiment, a therapy device for treating a tissue site is described. The therapy device may include a solution cartridge having a fluid reservoir, a raceway, and a tube suspended across the raceway. The therapy device may also include a cartridge receptacle adapted to receive the solution cartridge. The therapy device may further include a rotary-delivery pump head disposed within the cartridge receptacle. The rotary-delivery pump head may have a circumferential edge and lobes coupled to the circumferential edge. The circumferential edge may be adapted to press the tube into the raceway and the lobes are adapted to cyclically engage the tube in the raceway.

Other aspects, features, and advantages of the illustrative embodiments will become apparent with reference to the drawings and detailed description that follow.

BRIEF DESCRIPTION OF THE DRAWINGS

FIG. 9A is a sectional view of the solution cartridge of FIG. 8 taken along line 9A-9A of FIG. 8;

FIG. 9B is a sectional view of the solution cartridge of FIG. 8 taken along line 9B-9B of FIG. 8;

FIG. 9C is a sectional view of another example embodiment of the solution cartridge of FIG. 8 taken along line 9B-9B of FIG. 8;

FIG. 9D is a plan view of a port of the solution cartridge of FIG. 8;

DETAILED DESCRIPTION OF ILLUSTRATIVE EMBODIMENTS

New and useful systems, methods, and apparatuses for providing a combined solution pump and solution storage system for treating a tissue site are set forth in the appended claims. Objectives, advantages, and a preferred mode of making and using the systems, methods, and apparatuses may be understood by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments may also be described herein in the context of reduced-pressure therapy and instillation therapy applications, but many of the features and advantages are readily applicable to other environments and industries. Spatial relationships between various elements or the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
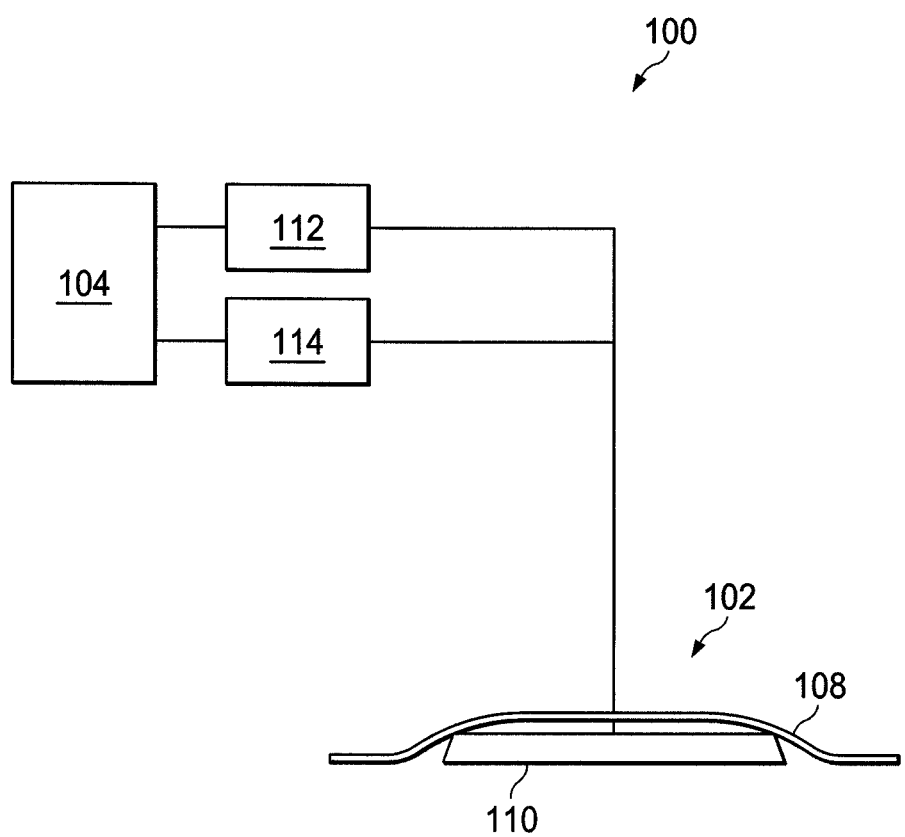
FIG. 1 is a functional block diagram of an example embodiment of a therapy system that can regulate therapeutic pressure and/or supply instillation solution in accordance with this specification.

FIG. 1 is a simplified functional block diagram illustrating details that may be associated with some embodiments of a therapy system 100. In some embodiments, the therapy system 100 can provide therapeutic pressure and/or instillation in accordance with this specification. In some embodiments, the therapy system 100 may include a dressing 102 fluidly coupled to a therapy device 104. The dressing 102 may include a drape, such as a drape 108, and a tissue interface, such as a manifold 110. The therapy system 100 may also include a fluid container, such as a container 112, and/or a solution cartridge, such as a cartridge 114. The container 112 may be fluidly coupled between the dressing 102 and the therapy device 104. The cartridge 114 may be fluidly coupled to the dressing 102 and operationally coupled the therapy device 104.

In general, components of the therapy system 100 may be coupled directly or indirectly to each other. For example, the therapy device 104 may be directly coupled to the container 112 and indirectly coupled to the dressing 102 through the container 112. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical union (such as a chemical bond) in some contexts.

In operation, a tissue interface, such as the manifold 110, may be placed within, over, on, against, or otherwise adjacent to a tissue site. For example, the manifold 110 may be placed against a tissue site, and the drape 108 may be placed over the manifold 110 and sealed to tissue proximate to the tissue site. Tissue proximate to a tissue site is often undamaged epidermis peripheral to the tissue site. Thus, the dressing 102 can provide a sealed therapeutic environment proximate to a tissue site, substantially isolated from the external environment, and the therapy device 104 can reduce the pressure in the sealed therapeutic environment. Reduced pressure can be distributed through the tissue interface across the tissue site in the sealed therapeutic environment to induce macrostrain and microstrain, as well as to remove exudates and other fluids from a tissue site, which can be collected in the container 112 and disposed of properly.

Exudates may refer to fluid that filters from the circulatory system into lesions or areas of inflammation. Exudates may include water and dissolved solutes. Dissolved solutes may include blood, plasma proteins, white blood cells, platelets, and red blood cells. In some embodiments, exudates may include serum, fibrin, and white blood cells. In other embodiments, exudates may include pus having a thin protein-rich fluid and dead leukocytes.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. Thus, in the context of reduced-pressure therapy, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. This orientation is generally presumed for purposes of describing various features and components of reduced-pressure therapy systems herein. However, the fluid path may also be reversed in some applications (such as by substituting a positive-pressure source for a reduced-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

"Reduced pressure" generally refers to a pressure less than a local ambient pressure, such as the ambient pressure in a local environment external to a sealed therapeutic environment provided by the dressing 102. In many cases, the local ambient pressure may also be the atmospheric pressure at which a patient is located. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The therapy device 104 may include a reduced-pressure source. A reduced-pressure source may be a reservoir of air at a reduced pressure, or may be a manual or electrically-powered device that can reduce the pressure in a sealed volume, such as a vacuum pump, a suction pump, a wall suction port available at many healthcare facilities, or a micro-pump, for example. A reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

The therapy device 104 may also include a fluid source. A fluid source may be a reservoir of fluid at an atmospheric or greater pressure, or may be a manual or electrically-powered device, such as a pump, that can convey fluid to a sealed volume, such as a sealed therapeutic environment, for example. In some embodiments, a fluid source may be a peristaltic pump. A peristaltic pump may include a circular pump casing having a rotor with one or more rollers. In some embodiments, a rotor may also be referred to as a pump head, and rollers may also be referred to as shoes, wipers, or lobes, for example. The rollers may be attached around a circumference of the rotor and positioned proximate to a section of tube. A peristaltic pump may further include a motor coupled to the rotor and configured to rotate the rotor so that the rollers engage the section of tube. As each roller engages the tube it may compress a portion of the tube, occluding the compressed portion of the tube. Rotation of the rotor may move the compressed location of the tube, pushing fluid through the tube ahead of the roller. In addition, as the tube opens after a roller passes, fluid may be drawn into the tube behind the roller. In this manner, fluid may be drawn into and moved through the tube. Generally, tubes engaged by a roller of a peristaltic pump may be formed of silicone.

A fluid source may be housed within or used in conjunction with other components, such as sensors, processing units, alarm indicators, memory, databases, software, display devices, or user interfaces that further facilitate instillation therapy. The amount and nature of the fluid applied to a tissue site may vary according to therapeutic requirements, which may include the size of the sealed therapeutic environment, the type of fluid, and any additives to the fluid. In some embodiments, the fluid may include: hypochlorite based solutions, such as hypochlorous acid and sodium hypochlorite; silver nitrate; sulfur based solutions, such as sulfonamides; biguanides, such as polyhexanide; cationic solutions, such as octenidine and benzalkonium chloride; and isotonic solutions.

The therapy device 104 may also include a user interface. A user interface may be a device configured to allow communication between a controller and an environment external to the therapy device 104. In some embodiments, an external environment may include an operator or a computer system configured to interface with the therapy device 104, for example. In some embodiments, a user interface may receive a signal from a controller and present the signal in a manner that may be understood by an external environment. In some embodiments, a user interface may receive signals from an external environment and, in response, send signals to a controller.

In some embodiments, a user interface may be a graphical user interface, a touchscreen, or one or more motion tracking devices. A user interface may also include one or more display screens, such as a liquid crystal display ("LCD"), lighting devices, such as light emitting diodes ("LED") of various colors, and audible indicators, such as a whistle, configured to emit a sound that may be heard by an operator. A user interface may further include one or more devices, such as knobs, buttons, keyboards, remotes, touchscreens, ports that may be configured to receive a discrete or continuous signal from another device, or other similar devices; these devices may be configured to permit the external environment to interact with the user interface. A user interface may permit an external environment to select a therapy to be performed with the therapy device 104. In some embodiments, a user interface may display information for an external environment such as a duration of the therapy, a type of therapy, an amount of reduced pressure being supplied, an amount of instillation solution being provided, a fluid level of a container, or a fluid level of a cartridge, for example.

The therapy device 104 may also include one or more pressure sensors. A pressure sensor may be a piezoresistive strain gauge, a capacitive sensor, an electromagnetic sensor, a piezoelectric sensor, an optical sensor, or a potentiometric sensor, for example. In some embodiments, a pressure sensor can measure a strain caused by an applied pressure. A pressure sensor may be calibrated by relating a known amount of strain to a known pressure applied. The known relationship may be used to determine an unknown applied pressure based on a measured amount of strain. In some embodiments, a pressure sensor may include a receptacle configured to receive an applied pressure.

The therapy device 104 may also include one or more valves. In some embodiments, for example, a valve may be fluidly coupled between a fluid reservoir and the dressing 102. A valve may be a device configured to selectively permit fluid flow through the valve. A valve may be a ball valve, a gate valve, a butterfly valve, or other valve type that may be operated to prevent or permit fluid flow through the valve. Generally, a valve may include a valve body having a flow passage, a valve member disposed in the flow passage and operable to selectively block the flow passage, and an actuator configured to operate the valve member. An actuator may be configured to position the valve member in a closed position, preventing fluid flow through the flow passage of the valve; an open position, permitting fluid flow through the fluid passage of the valve; or a metering position, permitting fluid flow through the flow passage of the valve at a selected flow rate. In some embodiments, the actuator may be a mechanical actuator configured to be operated by an operator. In some embodiments, the actuator may be an electromechanical actuator configured to be operated in response to the receipt of a signal input. For example, the actuator may include an electrical motor configured to receive a signal from a controller. In response to the signal, the electrical motor of the actuator may move the valve member of the valve. In some embodiments, a valve may be configured to selectively permit fluid communication between the therapy device 104 and the dressing 102.

The therapy device 104 may also include one or more flow meters. A flow meter may be a device configured to measure a fluid flow rate. A flow meter may include a mechanical flow meter, a pressure based flow meter, an optical flow meter, an open channel flow meter, a thermal mass flow meter, a vortex flow meter, electromagnetic, ultrasonic and coriolis flow meters, and laser doppler flow meters. The flow meter may determine a rate of fluid flow through the valve and transmit a signal to a controller corresponding to the determined flow rate.

The therapy device 104 may also include one or more controllers communicatively coupled to components of the therapy device 104, such as a valve, a flow meter, a sensor, a user interface, or a pump, for example, to control operation of the same. As used herein, communicative coupling may refer to a coupling between components that permits the transmission of signals between the components. In some embodiments, the signals may be discrete or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. An analog signal may be a continuous signal that includes a time varying feature that represents another time varying quantity. A digital signal may be a signal composed of a sequence of discrete values.

In some embodiments, the communicative coupling between a controller and other devices may be one-way communication. In one-way communication, signals may only be sent in one direction. For example, a sensor may generate a signal that may be communicated to a controller, but the controller may not be capable of sending a signal to the sensor. In some embodiments, the communicative coupling between a controller and another device may be two-way communication. In two-way communication, signals may be sent in both directions. For example, a controller and a user interface may be communicatively coupled so that the controller may send and receive signals from the user interface. Similarly, a user interface may send and receive signals from a controller. In some embodiments, signal transmission between a controller and another device may be referred to as the controller operating the device. For example, interaction between a controller and a valve may be referred to as the controller: operating the valve; placing the valve in an open position, a closed position, or a metering position; or opening the valve, closing the valve, or metering the valve.

A controller may be a computing device or system, such as a programmable logic controller, or a data processing system, for example. In some embodiments, a controller may be configured to receive input from one or more devices, such as a user interface, a sensor, or a flow meter, for example. In some embodiments, a controller may receive input, such as an electrical signal, from an alternative source, such as through an electrical port, for example.

In some embodiments, a controller may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, a controller may be a programmable logic controller (PLC). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

The therapy device 104 may also include a power source. A power source may be a device that supplies electric power to an electric load. A power source may include a battery, a direct current (DC) power supply, an alternating current (AC) power supply, a linear regulated power supply, or a switched-mode power supply, for example. A power supply may supply electric power to a controller, a sensor, a flow meter, a valve, a user interface, or a pump, for example.

A tissue interface, such as the manifold 110, can be generally adapted to contact a tissue site. A tissue interface may be partially or fully in contact with a tissue site. If a tissue site is a wound, for example, a tissue interface may partially or completely fill the wound, or may be placed over the wound. A tissue interface may take many forms, and may have many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

Generally, a manifold, such as the manifold 110, for example, is a substance or structure adapted to distribute or remove fluids across a tissue site. A manifold may include flow channels or pathways providing multiple openings that distribute fluids provided to and removed from a tissue site around the manifold. In one illustrative embodiment, the flow channels or pathways may be interconnected to improve uniformity of distribution of fluids provided to or removed from a tissue site. For example, open-cell foam, porous tissue collections, and other porous material such as gauze or felted mat generally include structural elements arranged to form flow channels. Liquids, gels, and other foams may also include or be cured to include flow channels.

In one illustrative embodiment, the manifold 110 may be a porous foam pad having interconnected cells adapted to distribute reduced pressure across a tissue site. The foam may be either hydrophobic or hydrophilic. In one non-limiting example, the manifold 110 can be an open-cell, reticulated polyurethane foam, such as GranuFoam® dressing available from Kinetic Concepts, Inc. of San Antonio, Tex.

In an example in which the manifold 110 may be made from a hydrophilic material, the manifold 110 may also wick fluid away from a tissue site, while continuing to distribute reduced pressure across the tissue site. The wicking properties of the manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site when pressure within the sealed therapeutic environment is reduced. For example, any or all of the surfaces of the manifold 110 may have an uneven, coarse, or jagged profile that can induce microstrains and stresses at a tissue site if reduced pressure is applied through the manifold 110.

In one embodiment, a tissue interface may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface may further serve as a scaffold for new cell-growth, or a scaffold material may be used in conjunction with a tissue interface to promote cell-growth. A scaffold is generally a biodegradable or biocompatible substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 is an example of a sealing member. A sealing member may be constructed from a material that can provide a fluid seal between two components or two environments, such as between a therapeutic environment and a local external environment. A sealing member may be, for example, an impermeable or semi-permeable, elastomeric film that can provide a seal adequate to maintain a reduced pressure at a tissue site for a given reduced-pressure source. For semi-permeable materials, the permeability of gas generally should be low enough that a desired reduced pressure may be maintained. An attachment device may be used to attach a sealing member to an attachment surface, such as undamaged epidermis, a gasket, or another sealing member. An attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

A "container," such as the container 112 broadly includes a canister, pouch, bottle, vial, or other fluid collection apparatus. The container 112 for example, can be used to manage exudates and other fluids withdrawn from a tissue site. In some embodiments, the container 112 may include substances to manage fluid in the container 112, such as isolyzers or absorbents, for example. In many environments, a rigid container may be preferred or required for collecting, storing, and disposing of fluids. In other environments, fluids may be properly disposed of without rigid container storage, and a re-usable container could reduce waste and costs associated with reduced-pressure therapy.

A "cartridge," such as the cartridge 114, is representative of another container, canister, pouch, or other storage component, which can be used to manage fluids, such as instillation solution, that can be supplied to the tissue site. In many environments a rigid container may be preferred or required for delivering, storing, and supplying of the instillation solution. In other environments, instillation solution may be provided in a non-rigid container. A re-usable container could reduce waste and costs associated with instillation.

In general, reduced-pressure therapy can be beneficial for wounds of all severity, but the cost and complexity of reduced-pressure therapy systems often limit the application of reduced-pressure therapy to large, highly-exudating wounds present on patients undergoing acute or chronic care, as well as other severe wounds that are not readily susceptible to healing without application of reduced pressure. Instillation of a fluid to a wound may further aid in healing of a wound. Instillation may include the slow introduction of a solution to the wound, for example. The solution may be used to provide moisture to the wound, to provide warmth or cold to the wound, to provide a drug to the wound, or to provide another substance to the wound. Often, each type of instillation therapy may require a different type of instillation fluid to achieve a desired effect. For example, a first type of fluid may provide moisture to the wound. A different type of fluid may supply a drug to the wound. Many times, the need for different fluid types to treat the wound may make instillation therapy time consuming to administer.

Some patients may experience improved outcomes with a combined treatment that includes using both reduced-pressure therapy and instillation therapy. Existing therapy systems that provide instillation or irrigation of a tissue site as well as reduced-pressure therapy can be complicated to use and setup. Multiple tubes, clamps, and interfaces may often be needed to properly apply both reduced pressure and fluid to the tissue site. For example, to set up a therapy system having both reduced-pressure therapy and instillation therapy, components for both systems may be placed proximate to a patient. The reduced-pressure therapy portion may need at least one tube set extending from the tissue site to the therapy system. In addition, floor space near the patient may be taken up by a separate collection container that may also require a separate tube set extending between the tissue site and/or the therapy device.

The instillation therapy system may need at least one intravenous pole to be placed near the patient. Another intravenous pole may be needed to support additional therapy devices. At least one, and often multiple, intravenous bags may be hung from the intravenous pole. Each bag hung from the intravenous pole may contain a different type of instillation fluid to apply a particular type of instillation fluid to the tissue site to achieve a desired effect. Each bag may need a separate tube set leading from the bag to the therapy device and from the therapy device to the tissue site. Each bag may also need clamps and valves for each tube set. As multiple bags, tube sets, clamps, and valves are added to the therapy system, the complexity increases. The increased complexity increases set up time for a caregiver and increases the likelihood that the caregiver administering therapy may incorrectly administer therapy.

As disclosed herein, the therapy system 100 can overcome these shortcomings and others by providing a combined solution pump and solution storage system. In addition, the therapy device 104 may place all components pertinent to the volumetric delivery of fluid into a single disposable assembly. The disposable assembly may interface with the therapy device 104 automatically if the disposable assembly engages the therapy device 104.

Figure 2:
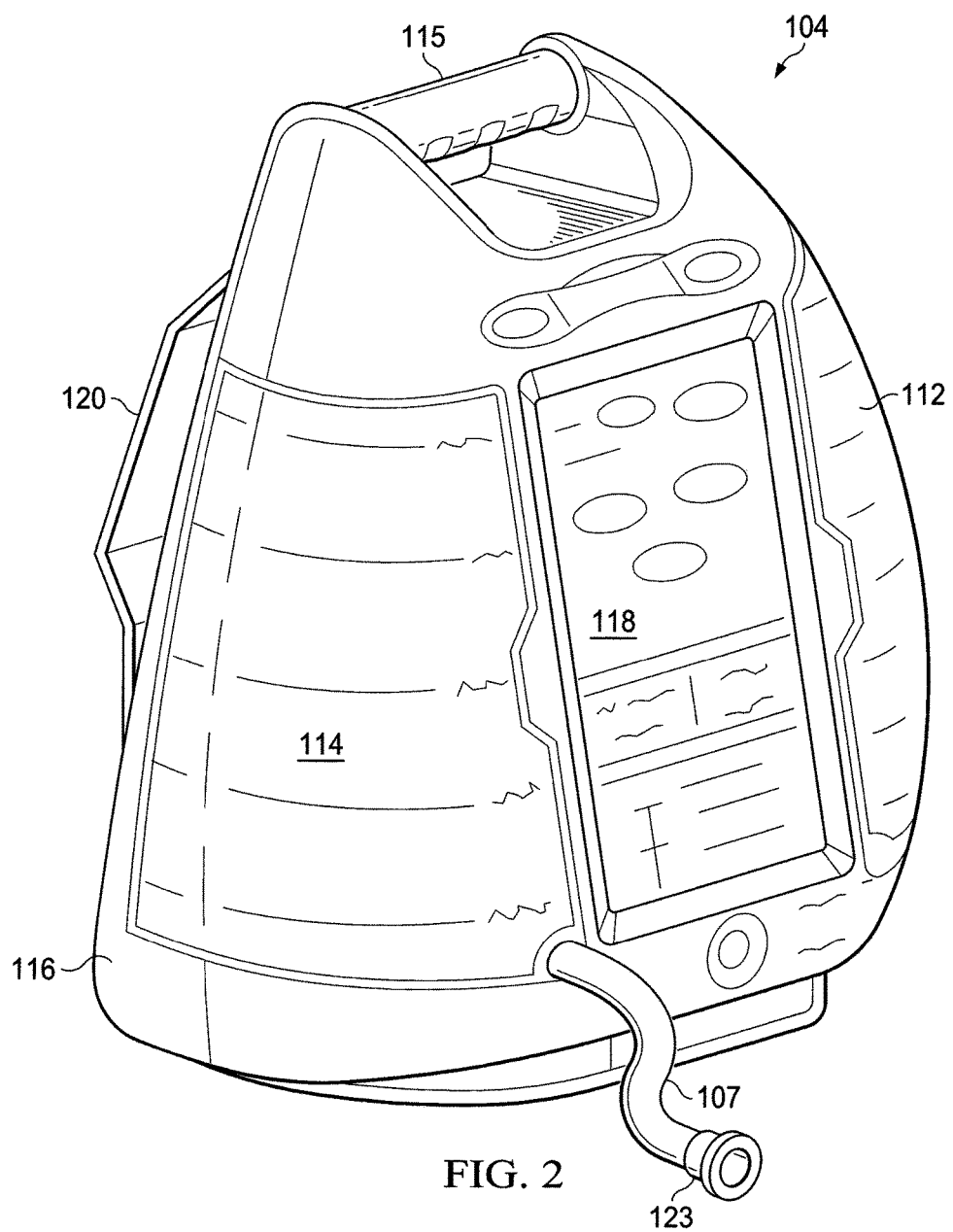
FIG. 2 is a perspective view of a therapy device with a solution cartridge installed in accordance with an illustrative embodiment.

FIG. 2 is a perspective view of the therapy device 104 illustrating details that may be associated with some embodiments. The therapy device 104 may have a base member, such as a body 116, a user interface panel, such as a panel 118, and a pole support, such as a support 120. The body 116 may be a housing, container, or other member configured to enclose components of the therapy device 104. In some embodiments, the body 116 may have an interior space into which pumps, tube, valves, electronics, controllers, regulators, metering devices, or sensors, for example, may be contained. The devices may be similar to and operate as described above to provide reduced-pressure therapy and/or instillation therapy. The body 116 may also include a handle 115. The handle 115 may be a portion of the body 116 configured to permit a caregiver to grip and carry the therapy device 104.

In some embodiments, the therapy device 104 may include the cartridge 114 and the container 112. Both the container 112 and the cartridge 114 may insert into the therapy device 104. In some embodiments, the container 112 and the cartridge 114 may placed into a front portion of the therapy device 104. As shown in FIG. 2, the therapy device 104 may include a tube 107 and a coupling 123. The tube 107 may protrude from a front of the therapy device 104 proximate to the cartridge 114. The coupling 123 may be fluidly coupled to the tube 107.

Figure 3:
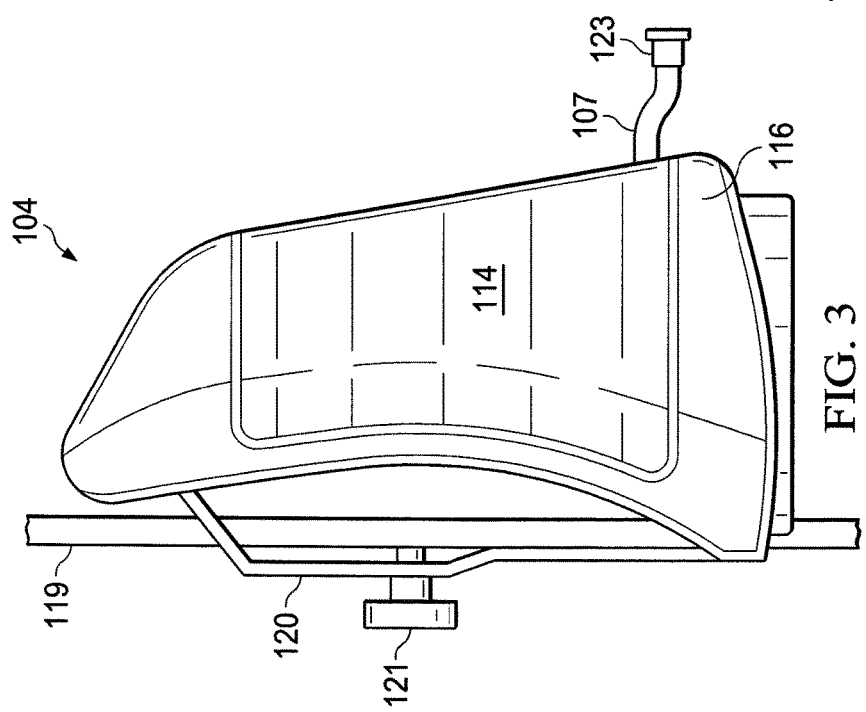
FIG. 3 is a side elevation of the therapy device of FIG. 2 with the solution cartridge installed.

FIG. 3 is a side view of the therapy device 104 illustrating additional details that may be associated with some embodiments. The support 120 may be a device configured for mounting of the therapy device 104 to a support, intravenous pole, or other device. In some embodiments, the support 120 may be configured to mount to an intravenous pole, such as a pole 119, for example. The support 120 may include a clamping device 121. In some embodiments, the clamping device 121 may be a threaded bolt having a handle. The bolt may be screwed into the support 120 so that an end of the threaded bolt of the clamping device 121 may be pressed against the pole 119. The clamping device 121 may compress the pole 119 against the support 120, preventing the support 120, and the therapy device 104, from moving relative to the pole 119. In other embodiments, the support 120 may include other devices to secure the therapy device 104 to the pole 119, such as latching mechanisms, tying mechanisms, or fusing mechanisms, for example.

Figure 4:
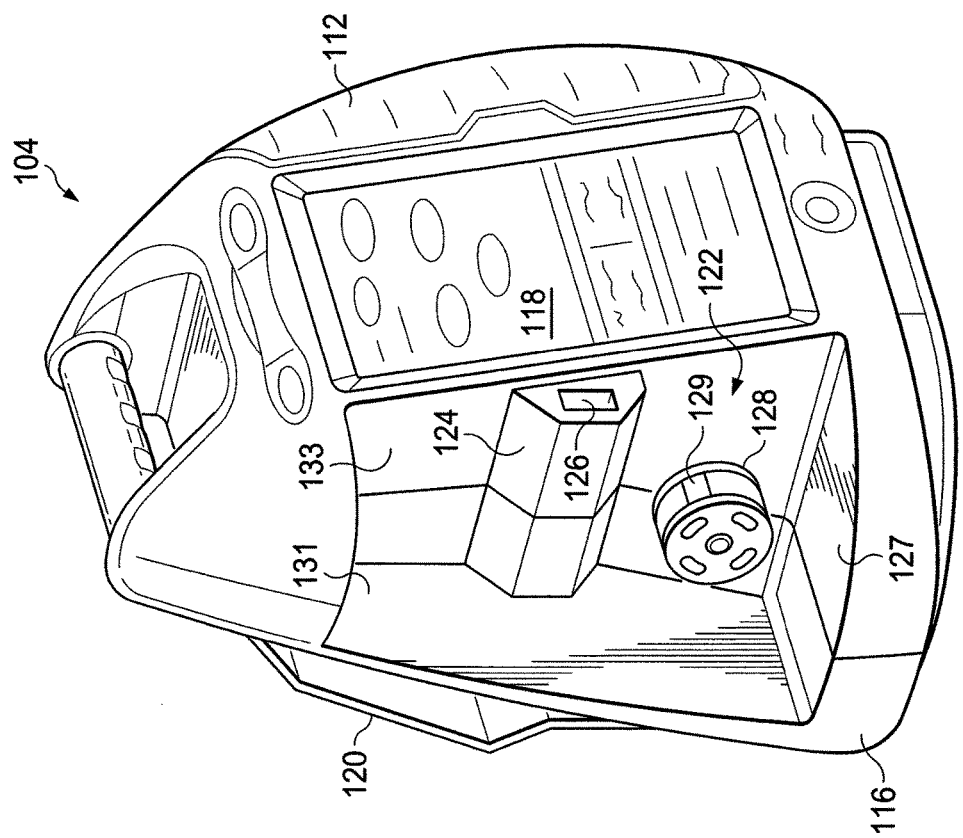
FIG. 4 is a perspective view of a portion of the therapy device of FIG. 2 having the solution cartridge removed.

FIG. 4 is a perspective view of the therapy device 104 illustrating additional details that may be associated with some embodiments. As shown, the cartridge 114 has been removed from the therapy device 104. In some embodiments, the therapy device 104 may include a cartridge receptacle 122. The cartridge receptacle 122 may be a cavity or other recessed portion of the therapy device 104. The cartridge receptacle 122 may be extend into the body 116 from a front of the body 116. In some embodiments, the cartridge receptacle 122 may have at least a bottom surface 127, a rear surface 131, and a side surface 133. In some embodiments, the bottom surface 127, the rear surface 131, and the side surface 133 are perpendicular to each other. In some embodiments, the cartridge receptacle 122 may be configured to receive the cartridge 114. For example, the cartridge receptacle 122 may have a size and shape so that the cartridge 114 may at least partially fit within the cartridge receptacle 122. In some embodiments, the cartridge 114 and the cartridge receptacle 122 may be sized so that if the cartridge 114 is inserted into the cartridge receptacle 122, an exterior surface of the cartridge 114 may be flush with an exterior of the therapy device 104 as shown in FIG. 2 and FIG. 3.

Referring to FIG. 4, in some embodiments, a key 124 may be positioned within the cartridge receptacle 122 on the side surface 133. In some embodiments, the key 124 may be disposed near a center of a height of the side surface 133. The key 124 may have a length equal to the length of the side surface 133 so that the key 124 extends from the front of the therapy device 104 to the rear surface 131. In some embodiments, the key 124 may protrude from the side surface 133 of the cartridge receptacle 122. In some embodiments, the key 124 may also include an opening 126. The opening 126 may be configured to receive a mating component of the cartridge 114, such as a latch, for example. In other embodiments, the mating component may be a tube component, a venting component, a sensing component, or a pump component, for example.

In some embodiments, a pump head 128 may be positioned within the cartridge receptacle 122. The pump head 128 may be positioned on the side surface 133 between the bottom surface 127 and the key 124. In some embodiments, the pump head 128 may be rotary-delivery pump head having a rotor with one or more rollers 129. As described above, the rollers 129 may be configured to engage a tube segment to move fluid through the tube segment using peristalsis. The pump head 128 may be coupled to operating components disposed within the body 116 of the therapy device 104. In some embodiments, the operating components may include motors, linking devices, or power sources, for example. The pump head 128 and the associated operating components may be disposed within the body 116 of the therapy device 104 and may be operatively or communicatively coupled to the panel 118. In some embodiments, the panel 118 may be manipulated by a caregiver to activate the pump head 128, causing the pump head 128 to rotate in a plane parallel to the side surface 133. As described above, rotation of the pump head 128 may move instillation solution from the cartridge 114 to the tissue site.

Figure 5:
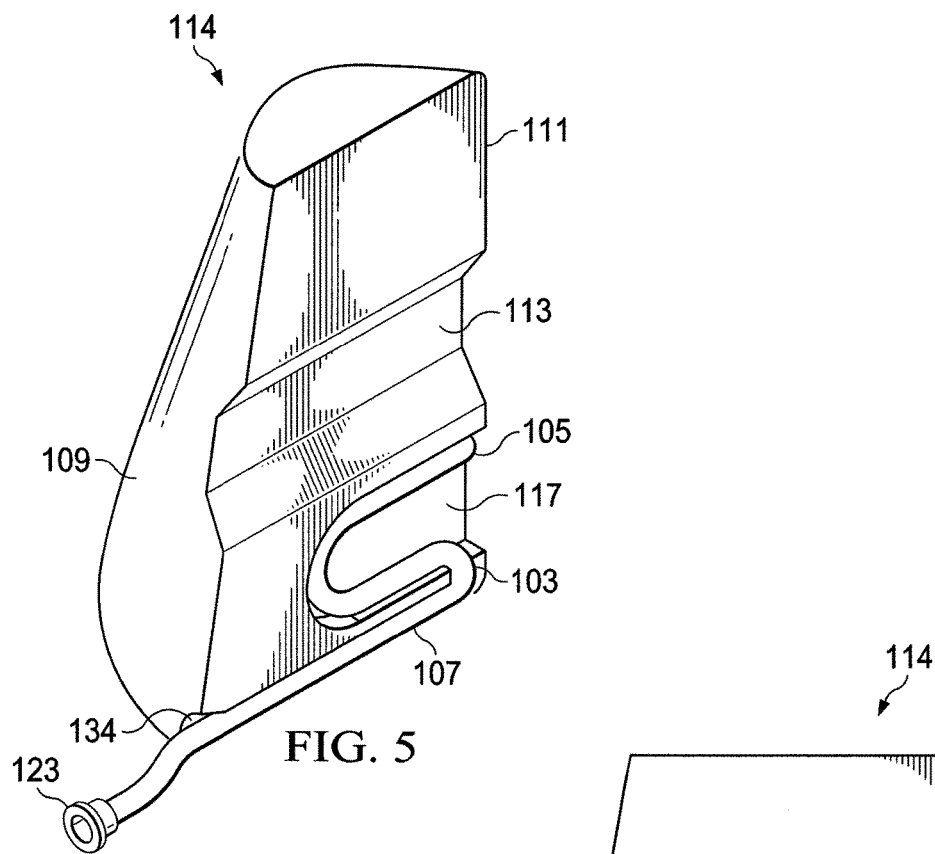
FIG. 5 is a perspective view of the solution cartridge of FIG. 2.
Figure 6:
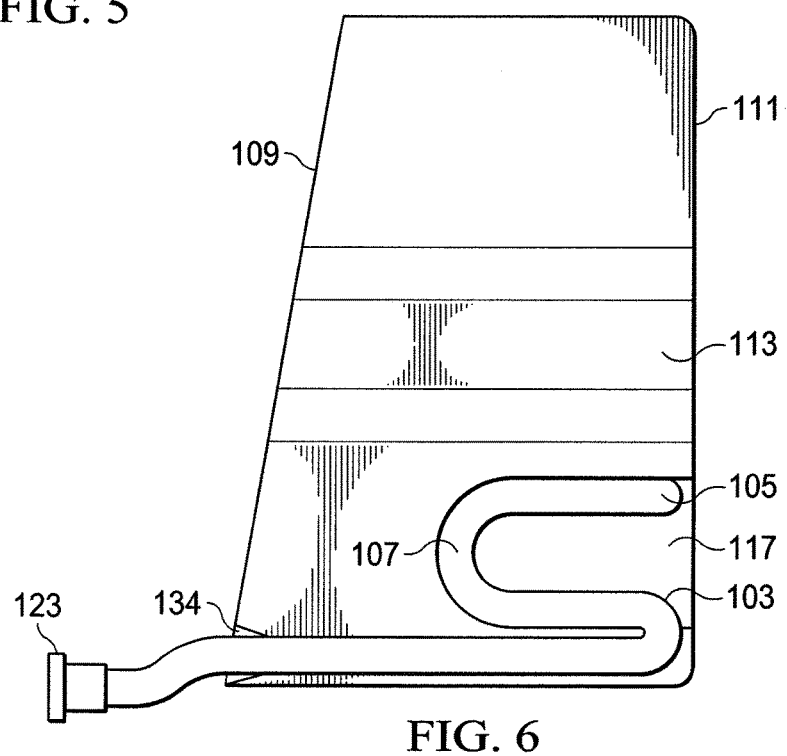
FIG. 6 is a side elevation of the solution cartridge of FIG. 5.

FIG. 5 is a perspective view of the cartridge 114 illustrating additional details that may be associated with some embodiments. FIG. 6 is a side elevation of the cartridge 114 in FIG. 5. The cartridge 114 may include a keyway 113. The keyway 113 may be a recessed portion of the cartridge 114. In some embodiments, the keyway 113 may be a slot or channel having a shape configured to receive the key 124 of the cartridge receptacle 122. In some embodiments, the keyway 113 may have a pentagonal shape to match the key 124. The keyway 113 may extend from a front 109 of the cartridge 114 to a back 111 of the cartridge 114.

The cartridge 114 may also include a tube housing 117. The tube housing 117 may be a recessed portion of the cartridge 114 extending from the back 111 of the cartridge 114 toward the front 109 of the cartridge 111. The tube housing 117 may be a generally rectangularly-shaped recess having a rounded end proximate to the front 109 of the cartridge 114. The rounded end of the tube housing 117 may be shaped to accommodate the tube 107. The tube 107 may have an end 105 fluidly coupled to an interior of the cartridge 114. The tube 107 may also have an elbow 103. In some embodiments, the elbow 103 may be a U-shaped elbow. In some embodiments, the tube housing 117 may be sized to receive the pump head 128. If the cartridge 114 is inserted into the cartridge receptacle 122, the pump head 128 may engage the tube 107 and be operable to compress the tube 107 against the tube housing 117 for peristaltic movement of fluid through the tube 107.

In some embodiments, the cartridge 114 may also include a tube channel 134. The tube channel 134 may be another recessed portion of the cartridge 114 that may be positioned between the tube housing 117 and a bottom of the cartridge 114. In some embodiments, the tube channel 134 may extend from the front 109 of the cartridge 114 to the back 111 of the cartridge 114. The tube channel 134 may be configured to accommodate at least a portion of a tube, such as the tube 107. In some embodiments, the elbow 103 may turn the tube 107 so that the tube 107 can be routed from the tube housing 117 to the tube channel 134 and protrude from the front 109 of the cartridge 114. In some embodiments, the tube 107 may be fluidly coupled to a union, such as the coupling 123, for example. The coupling 123 may be a device configured to fluidly couple the tube 107 to the tissue site. For example, the coupling 123 may be configured to be fluidly coupled to a tube that is fluidly coupled to the tissue site.

In operation, the cartridge 114 may be inserted into the therapy device 104. If the cartridge 114 is inserted into the cartridge receptacle 122, the key 124 and the keyway 113 may be aligned so that the key 124 may insert into the keyway 113. Alignment of the key 124 and the keyway 113 may align the tube housing 117 and the pump head 128. The pump head 128 may engage the tube 107 if the cartridge 114 is fully seated in the cartridge receptacle 122 of the therapy device 104. Operation of the pump head 128 may move fluid through the tube 107 from an interior of the cartridge 114 through the coupling 123.

Figure 7:
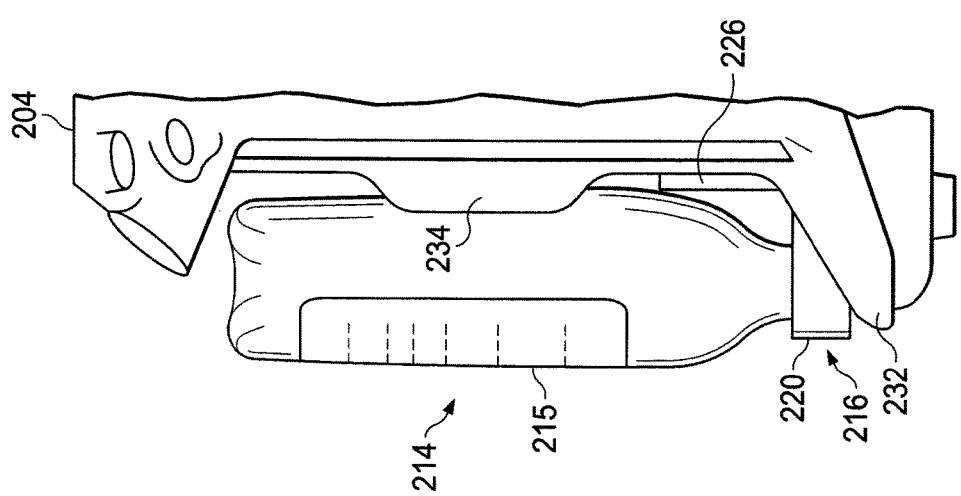
FIG. 7 is a side elevation of another solution cartridge installed in a therapy device.

FIG. 7 is an elevation view of a cartridge 214 illustrating details that may be associated with some embodiments. The cartridge 214 may be configured to engage a therapy device, for example a therapy device 204. In some embodiments, the therapy device 204 may be similar to and include the components of the therapy device 104. The therapy, device 204 may be configured to receive the cartridge 214. For example, the therapy device 204 may include a ledge 232 configured to support the cartridge 214 and one or more retainers 234 configured to limit lateral motion of the cartridge 214. In some embodiments, the cartridge 214 may include a fluid container 215 and a carrier 216. Generally, the fluid container 215 may interface with the carrier 216. The carrier 216 may interface with the therapy device 204 to secure the fluid container 215 to the therapy device 204 to provide instillation therapy. In some embodiments, the carrier 216 may be an integral component of the therapy device 204. In other embodiments, the carrier 216 may be an independent component of the therapy device 204.

Figure 8:
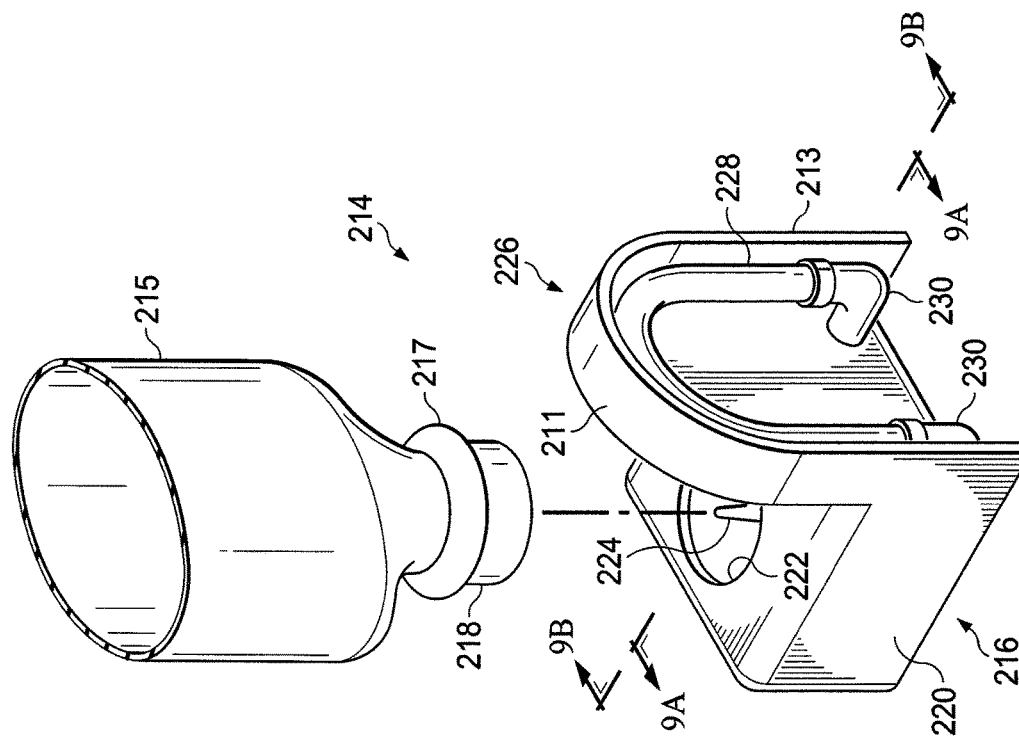
FIG. 8 is perspective view of the solution cartridge of FIG. 7.

FIG. 8 is a perspective view of the cartridge 214 illustrating additional details that may be associated with some embodiments. In some embodiments, the fluid container 215 may be a container configured to receive and store a fluid, such as an instillation fluid. In some embodiments, the fluid container 215 may be a refillable bottle or other device. In some embodiments, the fluid container 215 may be a pre-manufactured fluid container configured to engage the carrier 216. The fluid container 215 may have an open end and a closed end (not shown) opposite the open end. The open end of the fluid container 215 may be configured to receive a cap, coupling, or other similar device. In some embodiments, the fluid container 215 may have a port 218 coupled to the open end of the fluid container 215. The port 218 may be a device coupled to the open end of the fluid container 215 and configured to be selectively opened. In some embodiments, the port 218 may include a seal, such as a seal 217. The seal 217 may be a device configured to seal the fluid container 215 to another device or component. The seal 217 may be formed of a material, such as a rubber or other material configured to prevent fluid flow across the seal 217. In some embodiments, the seal 217 may be an O-ring. In some embodiments, the seal 217 may be separated from an end of the port 218. In other embodiments, the seal 217 may be proximate to an end of the port 218.

The carrier 216 may include a base housing 220 and a tube housing 226. The base housing 220 may be a rectangular body having a receptacle 222 and a venting spike 224 disposed in the receptacle 222. The receptacle 222 may be a recess disposed in a center of the base housing 220 that extends from a top of the base housing 220 toward a bottom of the base housing 220. In the illustrated embodiment, the receptacle 222 is cylindrical. In other embodiments, the receptacle 222 may have other sizes and shapes. Generally, the receptacle 222 may have a size, shape, and depth configured to mate with the port 218 so that the port 218 fits within the receptacle 222. The seal 217 may be configured to seal to the receptacle 222 if the port 218 is disposed in the receptacle 222. In other embodiments, the receptacle 222 may have a size, shape, and depth such that non-specific ports of other fluid containers may be inserted into the receptacle 222 to engage with the base housing 220 of the carrier 216.

In some embodiments, the tube housing 226 may couple to the base housing 220. The tube housing 226 may be a C-channel shaped piece coupled to a side of the base housing 220. In some embodiments, the tube housing 226 may form a wall perpendicular to the base housing 220 that extends upward beyond the surface of the base housing 220 in which the receptacle 222 is formed. An inner portion of the tube housing 226 may face away from the base housing 220. An upper end of the tube housing 226 may form an archway 211 between two sidewalls 213 of the channel-shaped piece. The inner portion may be disposed between the archway 211 and the two sidewalls 213 of the channel-shaped piece. In some embodiments, the tube housing 226 may have an open end opposite the archway 211.

The inner portion of the tube housing 226 may be configured to receive a tube 228. The tube 228 may have a first end and a second end opposite the first end. The ends of the tube 228 may be proximate to the open end of the tube housing 226. In some embodiments, the tube 228 may conform to the archway 211 of the tube housing 226. In some embodiments, the tube 228 may be in contact with the two sidewalls 213 and the archway 211 of the tube housing 226 along a length of the tube 228. The tube 228 may be coupled to the base housing 220 via elbow couplings 230. The elbow couplings 230 may be in fluid communication with the receptacle 222 or venting spike 224 and the tissue site.

FIG. 9A is a sectional view of the carrier 216 illustrating additional details that may be associated with some embodiments. As shown, an elbow 227 may be fluidly coupled to the elbow coupling 230 and the tube 228. The elbow 227 may provide a fluid coupling for another tube (not shown) that may be fluidly coupled to the tissue site. Fluid flowing from the fluid container 215 into the tube 228 in response to operation of the therapy device 204 may flow through the elbow coupling 230, the elbow 227, and to the tissue site.

FIG. 9B is another sectional view of the carrier 216 illustrating additional details that may be associated with some embodiments. FIG. 9B may be a reverse sectional view of the carrier 216 of FIG. 9A. The base housing 220 may include a coupling cavity 229 extending into the base housing 220 from a surface opposite the receptacle 222. In some embodiments, the coupling cavity 229 may have a major dimension, such as a diameter, that is greater than a major dimension of the receptacle 222. In some embodiments, the receptacle 222 and the coupling cavity 229 may be coaxial.

In some embodiments, the venting spike 224 may be disposed within the receptacle 222. The venting spike 224 may extend outwardly from an inner surface of the receptacle 222. In some embodiments, the venting spike 224 may have a wider portion where the venting spike 224 joins a surface of the receptacle 222 and tapers to a narrower portion at a distal end of the venting spike 224. The venting spike 224 may be configured to penetrate the port 218 if the port 218 of the fluid container 215 is inserted into the receptacle 222. For example, if the fluid container 215 is inverted and fitted into the receptacle 222 of the base housing 220, and the base housing 220 is secured to the therapy device 204, the venting spike 224 may breach the port 218. In some embodiments, the venting spike 224 may have a conduit 223. The conduit 223 may be in fluid communication with the coupling cavity 229. In some embodiments, the receptacle 222 may have a fluid passage 231 in fluid communication with an elbow 233. The elbow 233 may be fluidly coupled to the coupling 230 so that the elbow 233 is in fluid communication with the tube 228. In operation, the port 218 may be fitted into the receptacle 222 so that the venting spike 224 breaches into the port 218, and the conduit 223 may permit the flow of ambient air pressure into the fluid container 215. The venting spike 224 may form fluid paths in the port 218 adjacent to the venting spike 224. Fluid may flow from the fluid container 215 through the port 218 into the receptacle 222 around the venting spike 224. The fluid may flow through the fluid passage 231 into the elbow 233 and the tube 228 in response to operation of the therapy device 204. Ambient air pressure may flow through the conduit 223 into the fluid container 215 to prevent formation of a vacuum in the fluid container 215 during operation of the therapy device 204.

FIG. 9C is a sectional view of the carrier 216 illustrating additional details that may be associated with other embodiments. In other embodiments, the conduit 223 of the venting spike 224 may be fluidly coupled to an elbow 225. The elbow 225 may be fluidly coupled to the elbow coupling 230 so that the elbow 225 may be in fluid communication with the tube 228. Operation of the therapy device 204 may move fluid from the fluid container 215 through the conduit 223 of the venting spike 224, through the elbow 225 and the elbow coupling 230 and into the tube 228. In still other embodiments, the venting spike 224 may include multiple lumens to allow for both venting of the fluid container 215 and flow of the solution in the fluid container 215 into the therapy device 204.

FIG. 9D is a plan view of the port 218 illustrating additional details that may be associated with some embodiments. The port 218 may include a channel 219. The channel 219 may be an area of the port 218 configured to be breached by the venting spike 224. In some embodiments, the channel 219 may include tear lines 221. The tear lines 221 may be portions of the port 218 configured to open for flow of fluid if the venting spike 224 punctures the channel 219. In some embodiments, the tear lines 221 may be perforations in the port 218.

Figure 10:
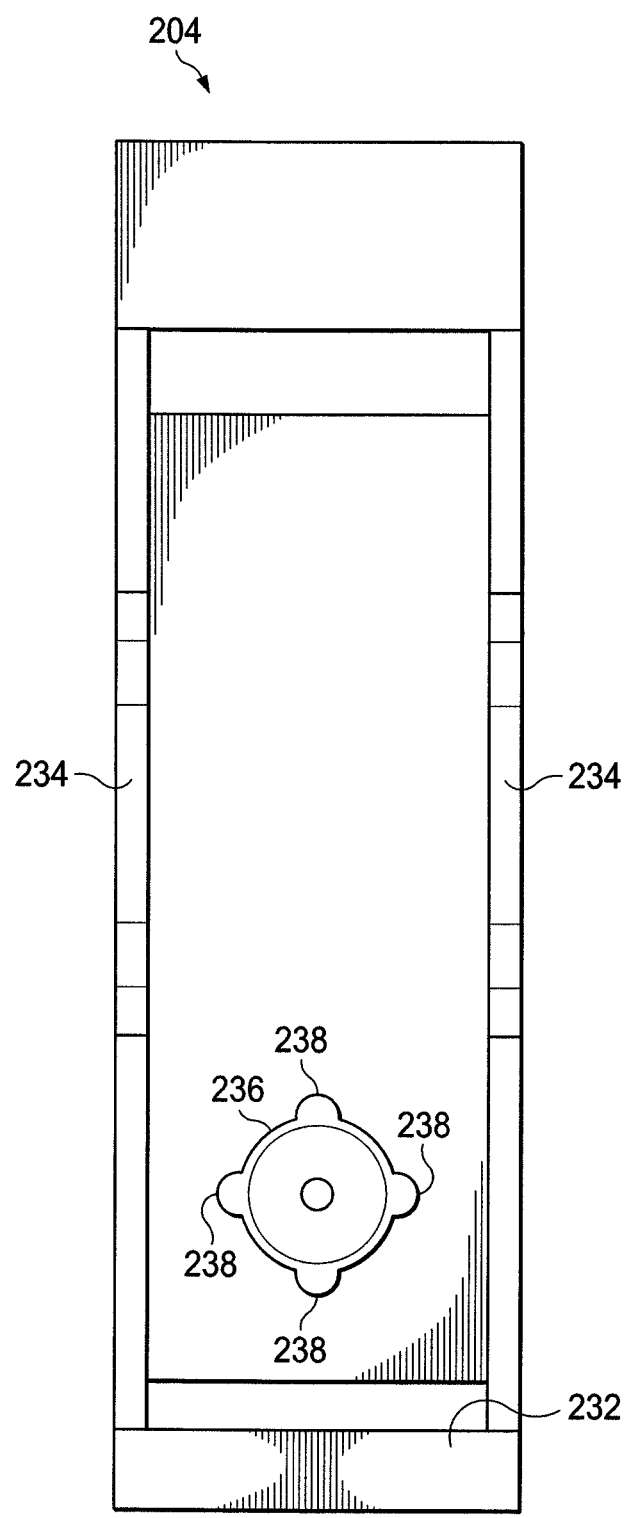
FIG. 10 is a side elevation of the therapy device of FIG. 7 having the solution cartridge removed.

FIG. 10 is a side elevation view of the therapy device 204 illustrating additional details that may be associated with some embodiments. As shown, the cartridge 214 has been removed from the therapy device 204. In some embodiments, the therapy device 204 may include a cartridge receptacle and a pump head. The cartridge receptacle may be formed by a ledge 232 and retainers 234. The ledge 232 may be a portion of the therapy device 204 extending away from the therapy device 204. The ledge 232 may provide a location onto which at least a portion of the cartridge 214 may be rested while the cartridge 214 is engaged with the therapy device 204. The retainers 234 may be elongated portions of the therapy device 204 that protrude from opposite sides of the therapy device 204. The retainers 234 may limit lateral motion of the cartridge 214 if the cartridge 214 is engaged with the therapy device 204. The pump head 236 may be a rotary-delivery pump head similar to the pump head 128 described above. The pump head 236 may include rollers or lobes 238 that may be configured to engage the tube 228 if the cartridge 214 is engaged with the therapy device 204. The pump head 236 may be positioned relative to the ledge 232 so that if the cartridge 214 is engaged with the therapy device 204, the pump head 236 and the lobes 238 engage the tube 228. In operation, the pump head 236 may be rotated, causing fluid to flow from the venting spike 224 or the receptacle 222 through the tube 228 and to the tissue site.

Figure 11:
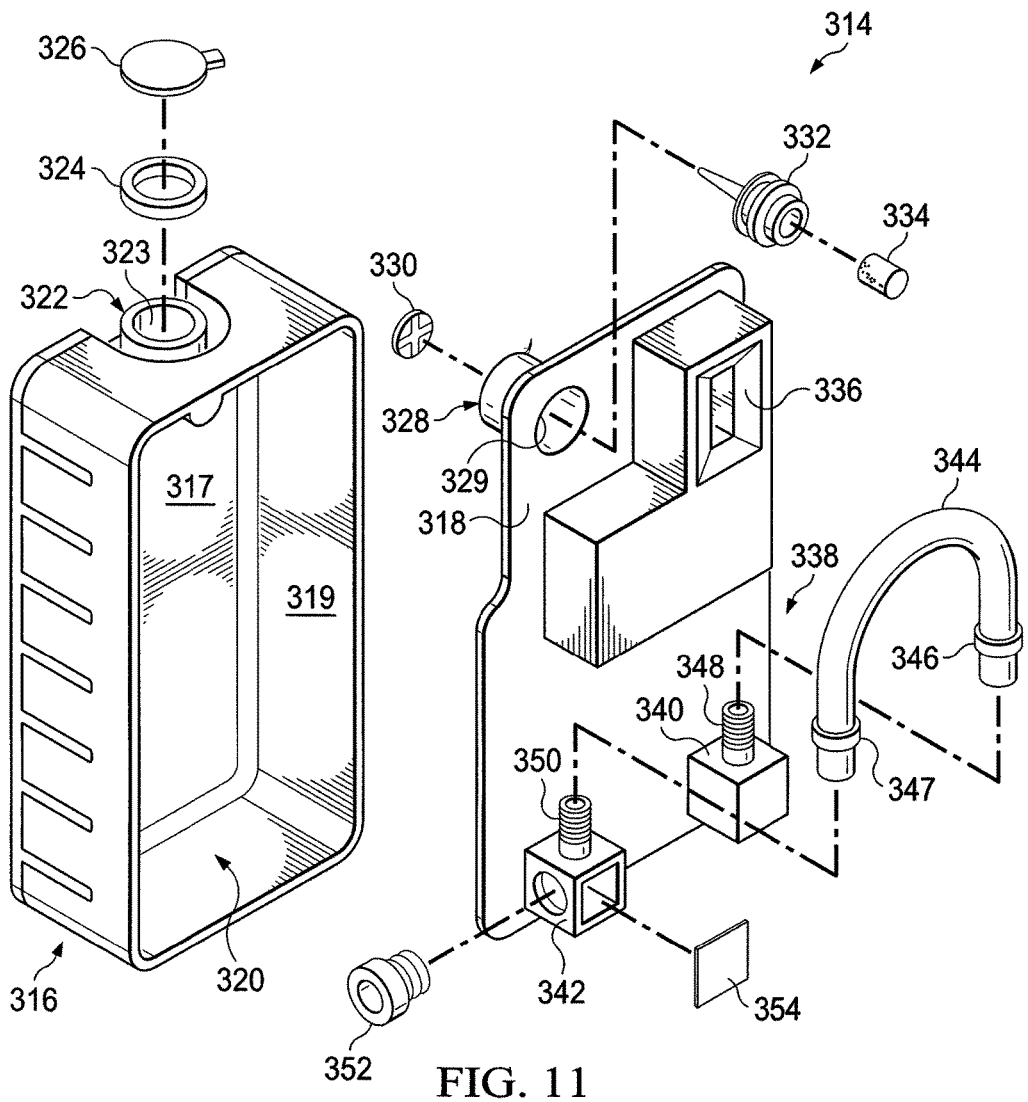
FIG. 11 is an exploded view of another example embodiment of a solution cartridge.

FIG. 11 is an exploded view of a cartridge 314 illustrating details that may be associated with some embodiments. The cartridge 314 may include a body 316 and a lid 318. The body 316 may be a rigid member having a rectangular shape as shown. In other embodiments, the body 316 may not be rigid and may have other shapes, such as triangular, circular, or amorphous shapes. In some embodiments, the body 316 may have a back 317 and walls 319. The body 316 may have a fluid reservoir 320 formed by the back 317 and the walls 319. The lid 318 may enclose the fluid reservoir 320. In some embodiments, the fluid reservoir 320 may be configured to receive and store instillation solution or other fluid for use with a therapy device, such as the therapy device 104 or the therapy device 204.

The body 316 may include a port 322 in one of the walls 319 of the body 316. In some embodiments, the port 322 may be a tubular body that mounts to one of the walls 319. The port 322 may have a central channel 323 that extends through the wall 319 so that the channel 323 is in fluid communication with the fluid reservoir 320. A cap mount 324 may be coupled to the port 322. In some embodiments, the cap mount 324 may be a rim coupled to the port 322 to provide a mounting surface for a cap 326. The cap 326 may be coupled to the cap mount 324 to prevent fluid communication through the port 322. The cap 326 may be coupled to the cap mount 324 following the filling of the fluid reservoir 320. In some embodiments, the cap 326 may be threaded, secured with adhesive, or otherwise latched to the cap mount 324. In some embodiments, the cap 326 may be a heat seal. A heat seal may be a cap welded to the cap mount 324 following filling of the fluid reservoir 320. The port 322, the cap mount 324, and the cap 326 may allow a manufacturer or pharmacist to fill the fluid reservoir 320 and then seal the fluid reservoir 320 for transport.

The lid 318 may be configured to mount and seal to the body 316 to form the fluid reservoir 320. The lid 318 may include a port 328. The port 328 may be a tubular body extending into the fluid reservoir 320 if the lid 318 is mounted to the body 316. The port 328 may include a channel 329 in fluid communication with the fluid reservoir 320. In some embodiments, a vent cap 330 may be coupled to the port 328. In some embodiments, a therapy device, such as the therapy device 104 or the therapy device 204, may include a venting spike 332. The vent cap 330 may block fluid flow through the port 328 until the cartridge 314 is engaged with a therapy device.

The lid 318 may also include a latch 336. The latch 336 may be disposed on the lid 318 so that the latch 336 is on an opposite side of the lid 318 from the fluid reservoir 320. The latch 336 may be configured to mate with a corresponding component on a therapy device, such as the key 124 of the therapy device 104, for example. If the latch 336 mates with the corresponding component of a therapy device, the latch 336 secures the cartridge 314 to the therapy device. In this manner, the cartridge 314 may be securely positioned on a therapy device while the therapy device instills an instillation solution or fluid from the fluid reservoir 320 to a tissue site.

In some embodiments, a tube assembly 338 may be coupled to the lid 318. The tube assembly 338 may include a first mount 340, a second mount 342, and a tube 344. The first mount 340 may be coupled to the lid 318 and include one or more channels providing a fluid path through the lid 318. If the lid 318 is mounted to the body 316, the channels may be in fluid communication with the fluid reservoir 320. A first barb 348 may be coupled to the first mount 340. The first barb 348 may be a tubular body having a channel in fluid communication with the channels of the first mount 340. The tube 344 may be a flexible tube having at least one lumen. The first barb 348 may be configured to be inserted into a first end of the tube 344 so that the tube 344 may be fluidly coupled to the first mount 340. A retaining collar 346 may be mounted on the tube 344. The retaining collar 346 may be placed over the portion of the tube 344 into which the first barb 348 was inserted. If the first barb 348 is inserted into the first end of the tube 344, the first end of the tube 344 may be expanded to accommodate the first barb 348. Thus, if the retaining collar 346 is placed over the portion of the tube 344 into which the first barb 348 was inserted, the retaining collar 346 may exert a frictional force on the tube 344 clamping the tube 344 to the first barb 348.

In some embodiments, the second mount 342 may be coupled to the lid 318 and include one or more channels providing a fluid path through the lid 318. If the lid 318 is mounted to the body 316, the channels may be in fluid communication with the fluid reservoir 320. A second barb 350 may be coupled to the second mount 342. The second barb 350 may be a tubular body having a channel in fluid communication with the channels of the second mount 342. The second barb 350 may be configured to be inserted into a second end of the tube 344 so that the tube 344 may be fluidly coupled to the second mount 342. A retaining collar 347 may be mounted on the tube 344. The retaining collar 347 may be placed over the portion of the tube 344 into which the second barb 350 was inserted. If the second barb 350 is inserted into the second end of the tube 344, the second end of the tube 344 may be expanded to accommodate the second barb 350. Thus, if the retaining collar 347 is placed over the portion of the tube 344 into which the second barb 350 was inserted, the retaining collar 347 may exert a frictional force on the tube 344 clamping the tube 344 to the second barb 350.

The tube 344 may arc between the first mount 340 and the second mount 342 so that a pump head, such as the pump head 128 of the therapy device 104, may be disposed under the tube 344 to engage the tube 344. If actuated by a therapy device, the pump head 128 may engage in peristalsis as described above to move fluid from the fluid reservoir 320 through the first mount 340, the tube 344, and the second mount 342 for fluid communication with a tissue site.

The second mount 342 may also include a valve connector 352. The valve connector 352 may be in fluid communication with the second mount 342 and the tube 344 through the second barb 350. The valve connector 352 may be configured to receive a tube that is in fluid communication with the tissue site. In some embodiments, the valve connector 352 may include a valve member that is positionable to selectively block fluid flow through the valve connector 352. In some embodiments, the valve connector 352 may be a check valve configured to permit fluid flow out of the second mount 342 and block fluid flow through the valve connector 352 into the second mount 342.

The second mount 342 may also include a pressure diaphragm 354 coupled to an outward facing portion of the second mount 342. The pressure diaphragm 354 may be a device configured to engage a corresponding sensor on a therapy device. The pressure diaphragm 354 may communicate a pressure in the second mount 342 to a therapy device. In some embodiments, a therapy device may receive a pressure signal from the pressure diaphragm 354 and, in response, adjust therapy.

Figure 12:
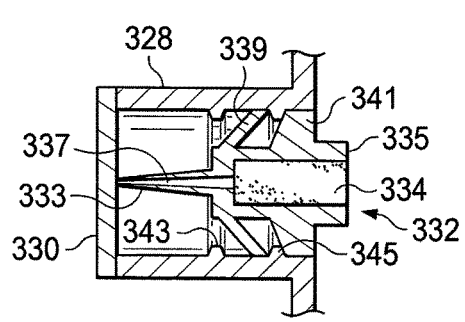
FIG. 12 and FIG. 13 are sectional views of a portion of a port of the solution cartridge of FIG. 11 having a venting spike disposed therein.

FIG. 12 is a sectional view of the venting spike 332 and the port 328 illustrating additional details that may be associated with some embodiments. The venting spike 332 may have a conical portion 333 and a base portion 335. The conical portion 333 may have a central channel 337 extending through the conical portion 333. The conical portion 333 may be coupled to the base portion 335. The conical portion 333 may have a wider portion adjacent to the base portion 335. The conical portion 333 may taper from the base portion 335 to a distal end. The conical portion 333 may be configured to penetrate the vent cap 330 if the vent cap 330 of the lid 318 is placed proximate to the venting spike 332, for example, if the cartridge 314 is engaged with a therapy device.

The base portion 335 may be a generally tubular body having a central channel having a filter 334 disposed within the channel. The filter 334 and the central channel 337 may be in fluid communication so that fluid may flow through the venting spike 332. The base portion 335 may include a first flange 339 and a second flange 341. The first flange 339 may be conical and extend away from the venting spike 332. The first flange 339 may be coupled to the venting spike 332 adjacent to a base of the conical portion 333. The second flange 341 may be coupled to a center of the base portion 335. The second flange 341 may have a conical surface proximate to the first flange 339 and a planar surface opposite the first flange 339.

In some embodiments, the port 328 may include one or more detents. For example, the port 328 may include a first detent 343, and a second detent 345. The first detent 343 may be an annular member disposed on an interior surface of the port 328 proximate to the vent cap 330. The second detent 345 may also be an annular member disposed on the interior surface of the port 328 between the first detent 343 and an end of the port 328 opposite the vent cap 330.

Figure 13:
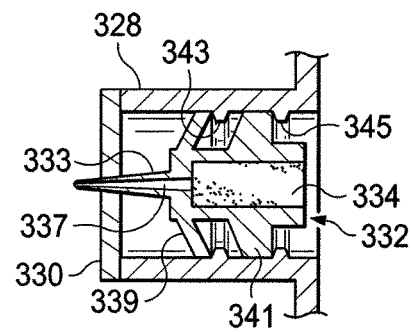

FIG. 13 is a sectional view of the port 328 and the venting spike 332 illustrating additional details that may be associated with some embodiments. As shown in FIG. 13, the first flange 339 and the second flange 341 may be configured to engage with the first detent 343 and the second detent 345 if the venting spike 332 is inserted into the port 328. In some embodiments, the conical portion 333 may pierce the vent cap 330, allowing fluid communication across the vent cap 330 through the venting spike 332. In some embodiments, the venting spike 332 may serve as a pathway for flow of ambient air pressure into the fluid reservoir 320 to prevent formation of a vacuum in the fluid reservoir 320 during operation of the therapy device.

Figure 14:
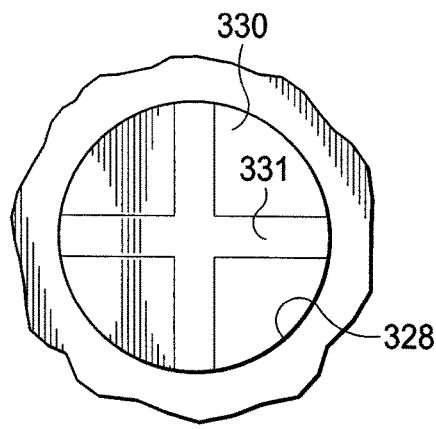
FIG. 14 is a plan view of a cap of the port of FIG. 12 and FIG. 13.

FIG. 14 is a plan view of the vent cap 330 illustrating additional details that may be associated with some embodiments. The vent cap 330 may include a channel 331. In some embodiments, the channel 331 may form a cross extending parallel to respective diameters of the vent cap 330. The channel 331 may be aligned with the venting spike 332 if the venting spike 332 is disposed within the port 328. The channel 331 may be a portion of the vent cap 330 that is more susceptible to penetration than remaining portions of the vent cap 330. In some embodiments, the channel 331 may be a portion of the vent cap 330 having a thickness that is less than a thickness of the remainder of the vent cap 330. In other embodiments, the channel 331 may be a portion of the vent cap 330 that has been treated to make the channel 331 more susceptible to penetration compared to the remaining portions of the vent cap 330.

Figure 15:
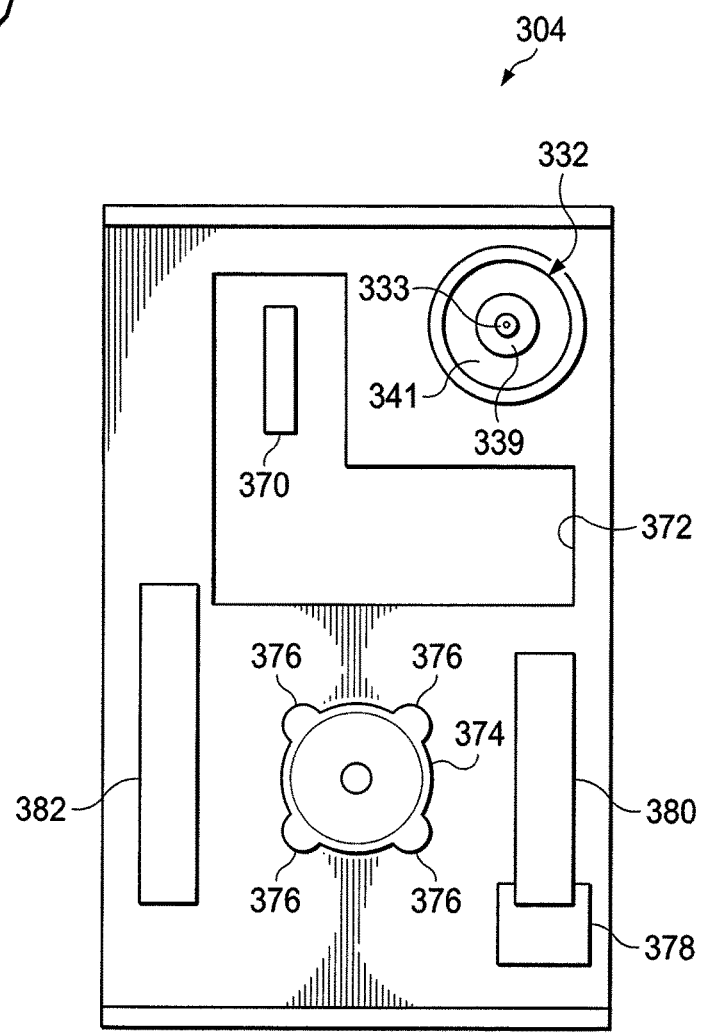
FIG. 15 is a side elevation of an example embodiment of a therapy device that may be used with the solution cartridge of FIG. 11.

FIG. 15 is a side elevation view of a therapy device 304 illustrating additional details that may be associated with some embodiments. As shown in FIG. 15, the venting spike 332 may be coupled to the therapy device 304. In some embodiments, the venting spike 332 may be positioned on the therapy device 304 so that if the cartridge 314 is engaged with the therapy device 304, the venting spike 332 may engage the port 328. The therapy device 304 may also include a striker 370. The therapy device 304 may also include a recessed portion 372 surrounding the striker 370. In some embodiments, the recessed portion 372 may be configured to receive at least a portion of the latch 336, so that the latch 336 and the striker 370 may engage one another if the cartridge 314 is engaged with the therapy device 304.

The therapy device 304 may also include a pump head 374 having one or more lobes 376. The pump head 374 may be similar to and operate as described above with respect to the pump head 128, and the pump head 236. Similarly, the lobes 376 may be similar to and operate as described above with respect to the rollers 129 and the lobes 238. In some embodiments, the pump head 374 may be positioned on the therapy device 304 so that the pump head 374 may engage the tube 344 if the cartridge 314 is engaged to the therapy device 304. The therapy device 304 may also include a pressure sensor 378. The pressure sensor 378 may be a sensor configured to engage the pressure diaphragm 354 to determine a pressure in the second mount 342. In some embodiments, the therapy device 304 may include a sensor 380 and a sensor 382. The sensor 380 and the sensor 382 may be positioned on the therapy device 304 to communicate with optional sensors that may be included on the cartridge 314.

Figure 16:
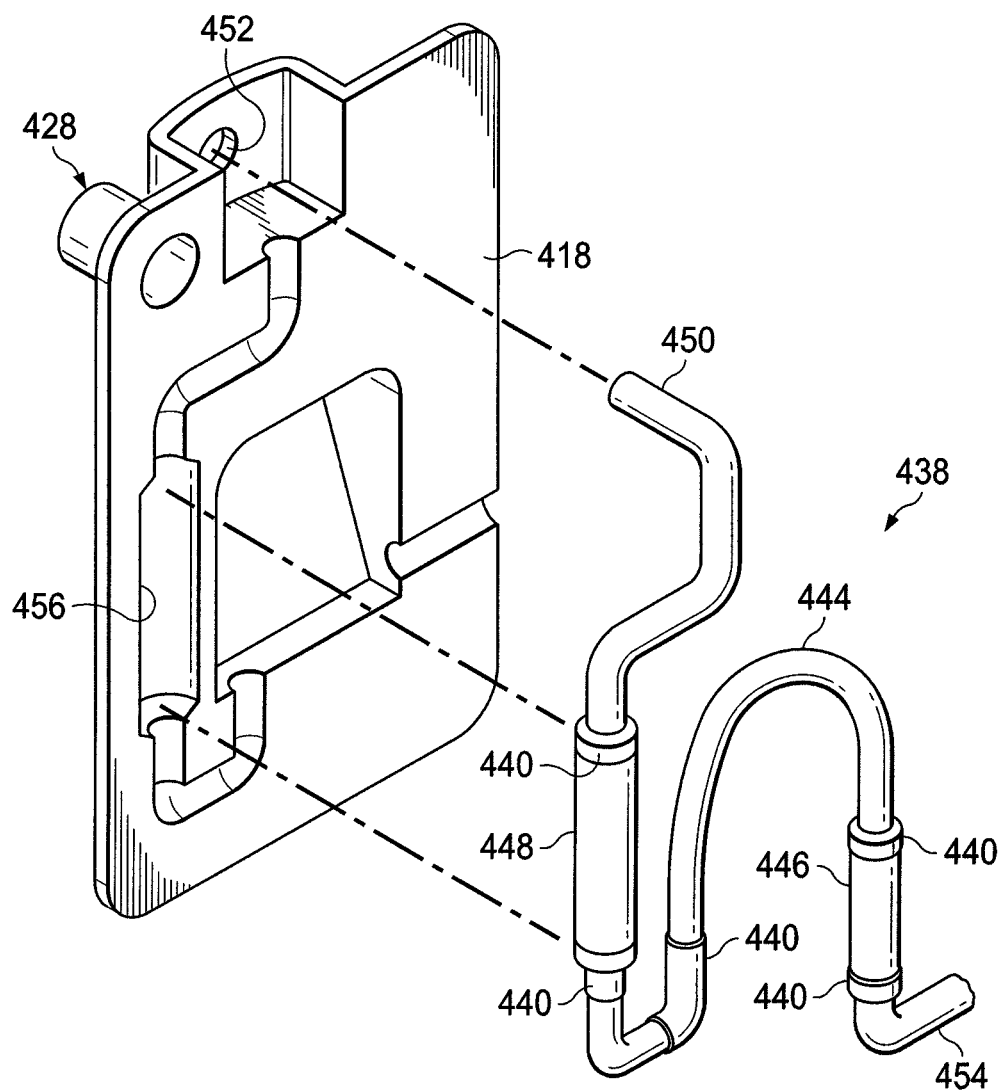
FIG. 16 is an exploded view of another example embodiment of a lid of the solution cartridge of FIG. 11.

FIG. 16 is an exploded view of a lid 418 illustrating details that may be associated with some embodiments of the cartridge 314 of FIG. 11. The lid 418 is similar to the lid 318 and may include the components thereof, modified as described below. The lid 418 may include a port 428 similar to the port 328. The port 428 may operate in a manner similar to the port 328. In some embodiments, the port 428 may be configured to receive the venting spike 332 as described above.

The lid 418 may also have a tube assembly 438. The tube assembly 438 may include a tube 450 and a plurality of couplings 440. The tube 450 may have a first end configured to pass through an aperture 452 formed in the lid 418. In some embodiments, the aperture 452 may be positioned on an end of the lid 418 proximate to the port 428. In some embodiments, the aperture 452 may be disposed in a recessed portion of the end of the lid 418. In some embodiments, the aperture 452 may be sized to accommodate the tube 450 while providing a seal to the tube 450. In some embodiments, the tube 450 may be in fluid communication with the fluid reservoir 320 through the aperture 452 in the lid 418. The tube 450 may include a segment (not shown) that extends from the aperture 452 to an end of the lid 418 that is opposite the aperture 452 so that an end of the tube 450 may be located proximate to a bottom of the fluid reservoir 320. The tube 450 may be have a lining of polyethylene. Lining the tube 450 with polyethylene may reduce reactions with fluid stored in the fluid reservoir 320. In some embodiments, additional tubes may be lined with polyethylene.

The tube assembly 438 may also include a tube 444, an ultra-sonic inspection segment 446, a load cell segment 448, and a tube 454. In some embodiments, the tube 450 is fluidly coupled to the load cell segment 448 with a coupling 440 so that fluid in the tube 450 may flow into the load cell segment 448. A load cell, such as the load cell segment 448, may be a transducer that converts a force into an electrical signal. A force applied through a load cell may deform a strain gauge, changing the electrical resistance of the strain gauge which may be interpreted by a controller or other device as an amount of force applied. In some embodiments, the load cell segment 448 may be configured to communicate with a corresponding sensor on a therapy device. For example, in some embodiments, the load cell segment 448 may communicate with the sensor 380 or the sensor 382 of the therapy device 304. In some embodiments, the load cell segment 448 may be configured to communicate with the sensor 380 if the cartridge 314, having the lid 418, is engaged with the therapy device 304. If fluid flows through the load cell segment 448, the fluid may exert a force on the load cell segment 448 that may generate a corresponding signal in the sensor 380. In this manner, the therapy device 304 may determine if there is fluid in the fluid reservoir 320. In some embodiments, the load cell segment 448 may also detect occlusion situations (blockages).

The load cell segment 448 may be fluidly coupled to the tube 444 through another coupling 440. In some embodiments, the coupling 440 may be an elbow coupling, such as the coupling 440 between the load cell segment 448 and the tube 444. The tube 444 may be fluidly coupled to the ultra-sonic inspection segment 446 with yet another coupling 440. The tube 444 may be positioned to form an arc so that the tube 444 may receive a pump head, such as the pump head 374 of the therapy device 304. If actuated by a therapy device 304, the pump head 374 may engage in peristalsis to move fluid from the fluid reservoir 320 through the tube 444 for fluid communication with a tissue site as described above.

In some embodiments, the ultra-sonic inspection segment 446 may be a device configured to use ultrasound to monitor the fluid reservoir 320. The ultra-sonic inspection segment 446 may be configured to communicate with a therapy device, such as the therapy device 304. For example, if the cartridge 314 having the lid 418 is engaged with the therapy device 304, the ultra-sonic inspection segment 446 may be in communication with the sensor 382. The ultra-sonic inspection segment 446 may also detect occlusion situations (blockages).

The ultra-sonic inspection segment 446 may be fluidly coupled to another tube 454 with another coupling 440. The tube 454 may have a coupling on an end of the tube 454 opposite the ultra-sonic inspection segment 446. In this manner, the tube 454 may be used to fluidly couple the cartridge 314 having the lid 418 to a dressing and a tissue site.

The lid 418 includes a recess 456 molded into the lid 418. The recess 456 may be shaped to accommodate the connection of the tube assembly 438 so that the tube assembly 438 is flush with, or at least partially recessed from an exterior surface of the lid 418. A portion of recess 456 may be sized to receive a pump head, such as the pump head 374 of the therapy device 304 so that the exterior surface of the lid 418 is flush with the therapy device if the cartridge 314 is engaged with the therapy device 304.

Figure 17:
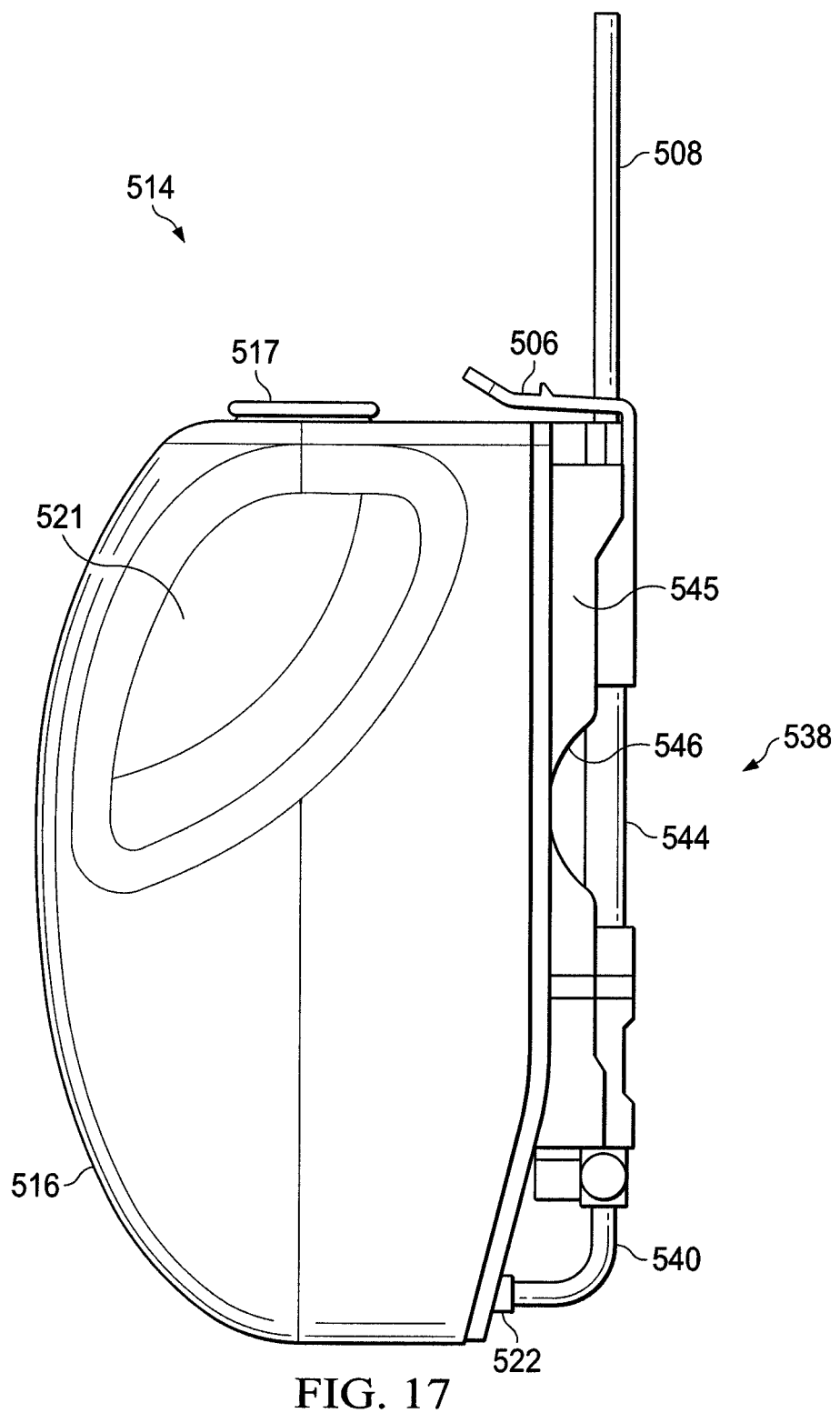
FIG. 17 is a side elevation of another embodiment of a solution cartridge.

FIG. 17 is an elevation of another example embodiment of a cartridge 514 that may be used with a therapy device, such as the therapy device 104, the therapy device 204, or the therapy device 304, modified as described below. The cartridge 514 may be similar in many respects to the cartridge 114, the cartridge 214, and the cartridge 314. The cartridge 514 may include a shell 516. In some embodiments, the shell 516 is at least partially ovoid-shaped having a rounded end and a flattened end opposite the rounded end. In some embodiments, the rounded end is a lower end configured to engage a portion of a therapy device to at least partially secure the cartridge 514 to the therapy device. The shell 516 also may include notches 521. The notches 521 may be molded recesses formed in a portion of the shell 516 proximate to the flattened end. The notches 521 may provide a handle portion configured to allow a person to grip the cartridge 514 for engagement and disengagement with a therapy device.

In some embodiments, the shell 516 may include an aperture 517 through the flattened end of the shell 516. The aperture 517 can provide fluid communication between an exterior of the cartridge 514 and an interior of the cartridge 514. The cartridge 514 may also include a port 522. In some illustrative embodiments, a filter may be disposed in the port 522 to prevent bacteria, viruses, and other undesirable materials from entering the cartridge 514.

In some embodiments, the cartridge 514 also has a tube assembly 538, which may be similar to the tube assembly 338 or the tube assembly 438. The tube assembly 538 may include suitable connectors, such as an elbow 540, and a tube 544. In some embodiments, the tube assembly 538 may be fluidly coupled to a conduit 508, which may be adapted for coupling to a dressing. As illustrated, the tube 544 may extend across a raceway 546. The tube assembly 538 is configured to engage a pump head of a therapy device, so that the pump head may cause instillation solution disposed within the cartridge 514 to flow through the tube assembly 538 and the conduit 508 to a tissue site as described above.

Figure 18:
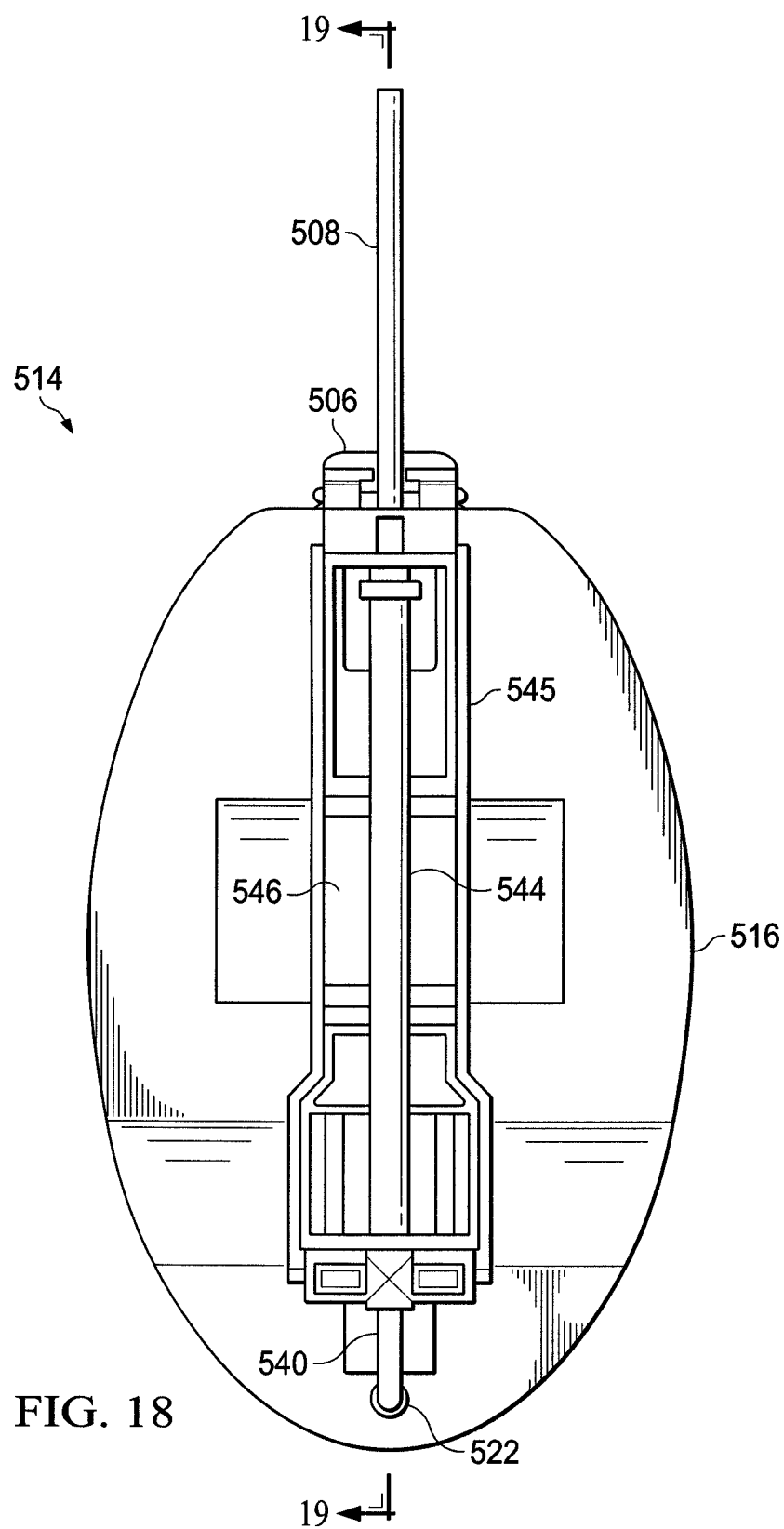
FIG. 18 is a rear elevation of the solution cartridge of FIG. 17.

FIG. 18 is an elevation of a second side of the cartridge 514 illustrating additional details that may be associated with some embodiments. In some embodiments, the raceway 546 may be a cavity in the shell 516 adapted to receive a circumferential edge of a rotary-delivery pump head (not shown). In some embodiments, the raceway 546 may be a portion of amount 545. The mount 545 may be a device coupled to the shell 516 and configured to position the tube assembly 538 to receive a pump head. The mount 545 may also include a latch 506. The latch 506 may be positioned adjacent to the flattened end of the shell 516. The latch 506 may be configured to engage a portion of a therapy device to secure the cartridge 514 to the therapy device.

Figure 19:
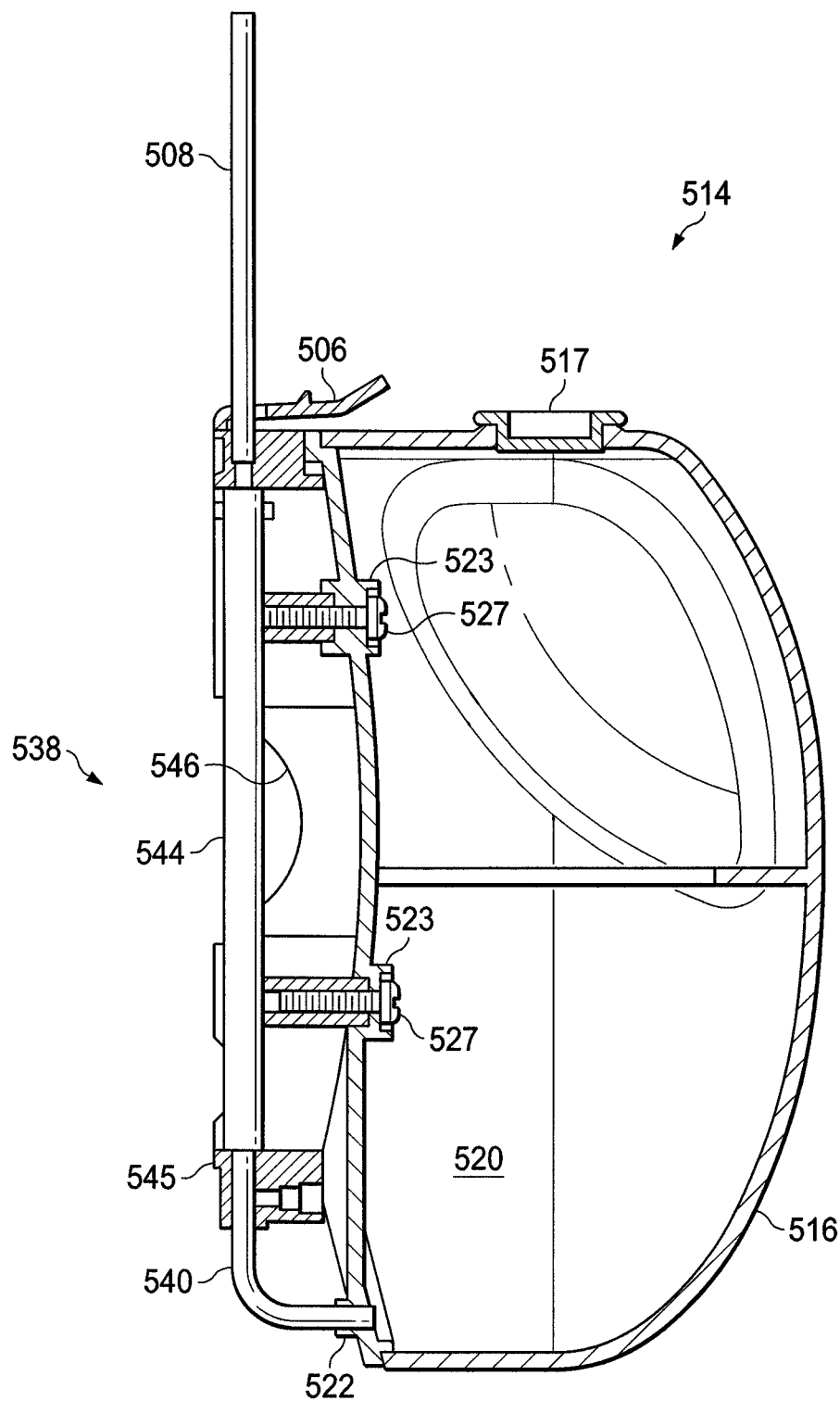
FIG. 19 is a sectional view of the solution cartridge of FIG. 18 taken along line 19-19.

FIG. 19 is a cross-sectional view of the cartridge 514 illustrating additional details that may be associated with some embodiments. The shell 516 may form a fluid reservoir 520, similar to the fluid reservoir of the cartridge 114, the fluid container 215, and the fluid reservoir 320. In some embodiments, the shell 516 may include mounting locations 523 configured to receive fasteners 527 to secure the shell 516 to the mount 545. The fasteners 527 may seal to the shell 516 to prevent leakage of fluid through the mounting locations 523.

The cartridge 514 may be positioned to engage with and interact with a pump head. The raceway 546 may be a semicircular cavity, and tube 544 may be suspended across the cavity. In more particular embodiments, the raceway 546 may be a cavity with an arc of about 180 degrees. For example, the tube 544 and the raceway 546 may be aligned with and disposed on a circumferential edge of a rotary-delivery pump head. Thus, the tube 544 is disposed between raceway 546 and the edge of a pump head. The tube 544 may be stretched and pressed into and against raceway 546 by a pump head.

In some embodiments, the latch 506 may be a spring loaded mechanism configured to engage a mating component of a therapy device. In some embodiments, the latch 506 may include buttoning mechanisms, threaded mechanisms, clip mechanisms, or friction engagement mechanisms, for example. In some embodiments, the latch 506 may be disposed on the cartridge 514 and engage a mating element, such as a notch, clip, or threaded coupler, for example, on a therapy device.

Figure 20:
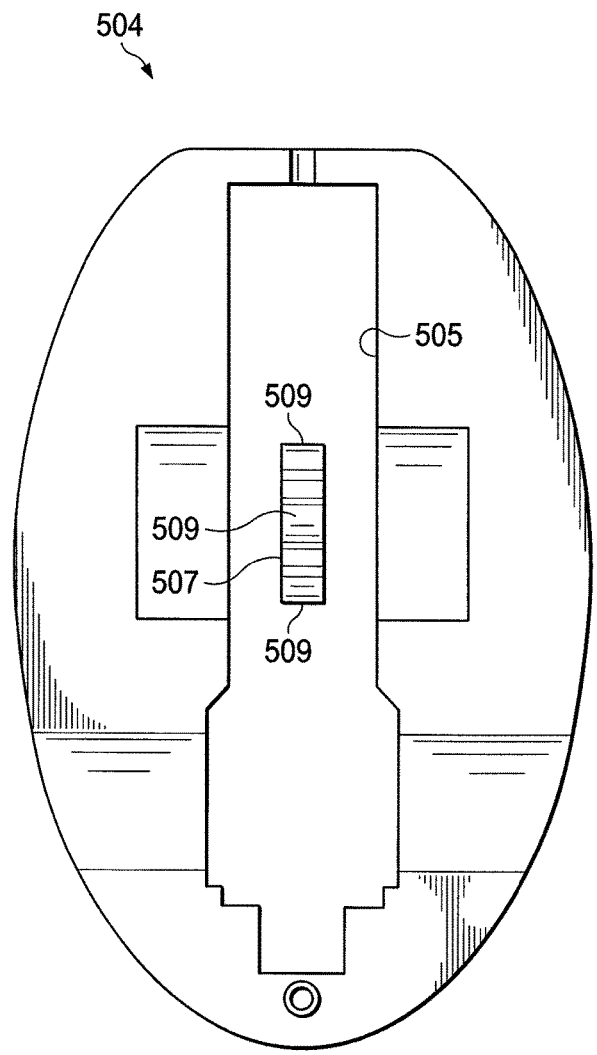
FIG. 20 is a side elevation of a therapy device that may be used with the fluid container of FIG. 17.
Figure 21:
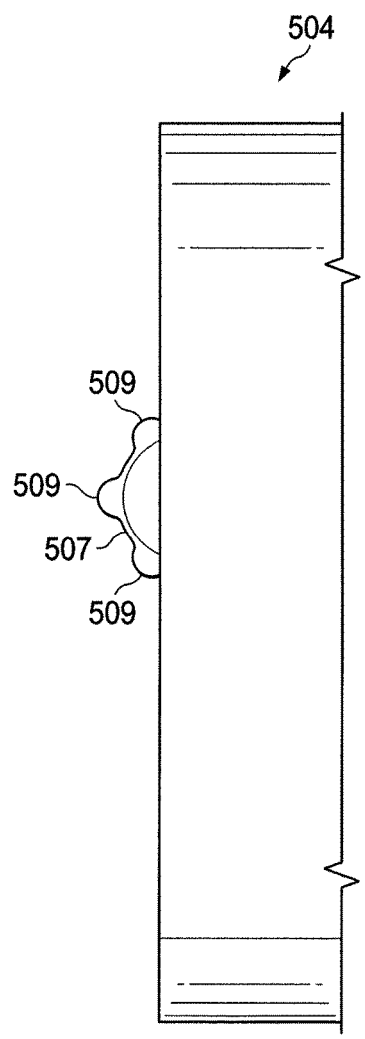
FIG. 21 is a partial front elevation of the therapy device of FIG. 20.

FIG. 20 is a side elevation of a therapy device 504 illustrating details that may be associated with some embodiments. FIG. 21 is a partial front elevation of the therapy device 504 illustrating additional details that may be associated with some embodiments. The therapy device 504 may be similar to the therapy device 104, the therapy device 204, and the therapy device 304, modified as described herein. The therapy device 504 may have outer dimensions similar to the outer dimensions of the cartridge 514 proximate to the mount 545. In some embodiments, if the cartridge 514 is engaged with the therapy device 504, the edges of the therapy device 504 may be flush with the edges of the cartridge 514. In some embodiments, the therapy device 504 may include a recess 505. The recess 505 may have a shape configured to receive the mount 545. In some embodiments, the recess 505 may include a counterpart to the latch 506 proximate to a flattened end of the therapy device 504 that is configured to engage the latch 506.

In some embodiments, the therapy device 504 may also include a pump head 507 having one or more lobes 509. The pump head 507 may be similar to the pump head 128, the pump head 236, and the pump head 374. In some embodiments, the pump head 507 may be oriented perpendicular to a plane containing a side surface of the therapy device 504. In this manner, the pump head 507 may protrude from the recess 505 of the therapy device 504.

In operation, the therapy device 504 may rotate the pump head 507, and the lobes 509 attached to the external circumference of the pump head 507 may cyclically engage and compress the tube 544. As the pump head 507 turns, the part of the tube 544 under compression is occluded, which can force fluid through the tube 544. Additionally, as the tube 544 opens after a lobe 509 passes, fluid may be drawn into the tube 544 from the fluid reservoir 520 through the port 522 and elbow 540. Thus, in the illustrative embodiment of FIGS. 17-21, fluid may be cyclically drawn in from a bottom portion of the fluid reservoir 520 and pumped upwards through tube assembly 538 to conduit 508.

The systems and methods described herein may provide significant advantages, some of which have already been mentioned. For example, the therapy system 100 minimizes usability problems in clinical care settings by replacing hanging irrigation bags and bottles on intravenous poles. The system provides the installation solution via a solution cartridge that minimizes intravenous bags and the confusion associated with the device placement and setup of the same. Still further the system can decrease the amount of time required to setup and change canisters. The system can also provide volumetric delivery of installation solution (via a solution cartridge) with a negative wound pressure therapy device. Specifically, the system allows for a rotary-delivery pump (located on the device) to engage a disposable cartridge that contains an installation solution.

Although certain illustrative, non-limiting embodiments have been presented, it should be understood that various changes, substitutions, permutations, and alterations can be made without departing from the scope the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, features of any of the embodiments described above may be combined with features of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A therapy device for instillation of fluid to a tissue site, the therapy device comprising:
    a base having a cartridge receptacle configured to receive a cartridge;
    the cartridge separable from the base and configured to engage the base when positioned in the cartridge receptacle, the cartridge comprising:
        a body having a raceway recessed therein, wherein the body and the raceway form at least a portion of a fluid reservoir,
        a tube segment coupled to the body and having a tube suspended across the raceway, the tube in fluid communication with the fluid reservoir; and
    a pump head having a roller and at least one lobe, the pump head disposed within the cartridge receptacle and configured to engage the tube for movement of fluid.

2. The therapy device of claim 1, further comprising a fill port fluidly coupled to the fluid reservoir and configured to receive fluid.

3. The therapy device of claim 1, further comprising a fill port fluidly coupled to the fluid reservoir and configured to receive fluid; and
    a heat seal coupled to the fill port.

4. The therapy device of claim 1, further comprising:
    a load cell segment fluidly coupled to the tube segment between an end of the tube segment and the fluid reservoir; and
    a sensor coupled to the base and configured to communicatively couple to the load cell segment if the cartridge is disposed in the cartridge receptacle.

5. The therapy device of claim 1, further comprising:
    an ultra-sonic inspection segment fluidly coupled to the tube segment between an end of the tube segment and the tissue site; and
    a sensor coupled to the base and configured to communicatively couple to the ultra-sonic inspection segment if the cartridge is disposed in the cartridge receptacle.

6. The therapy device of claim 1, wherein the body comprises a lid configured to form at least a portion of the fluid reservoir.

7. The therapy device of claim 1, wherein the body comprises a lid configured to form at least a portion of the fluid reservoir, the raceway is in the lid, and the raceway is configured to receive at least a portion of the tube segment and the pump head.

8. The therapy device of claim 1, wherein the body has an ovoid-shape with a rounded end and a flattened end opposite the rounded end.

9. The therapy device of claim 1, wherein the body has an ovoid-shape with a rounded end and a flattened end opposite the rounded end, the body having at least one notch proximate to the flattened end.

10. The therapy device of claim 1, wherein the raceway comprises a semicircular raceway.

11. The therapy device of claim 1, further comprising an interactive panel coupled to the base and operatively coupled to the pump head for operation thereof.

12. A therapy device for treating a tissue site, the therapy device comprising:

a solution cartridge separable from the therapy device and comprising a fluid reservoir, a raceway forming at least a portion of the fluid reservoir, and a tube suspended across the raceway;

a cartridge receptacle formed in the therapy device and adapted to receive the solution cartridge; and a rotary-delivery pump head disposed within the cartridge receptacle, the rotary-delivery pump head having a circumferential edge and lobes coupled to the circumferential edge;

wherein the circumferential edge is adapted to press the tube into the raceway and the lobes are adapted to cyclically engage the tube in the raceway.

13. The therapy device of claim 12, further comprising a dressing fluidly coupled to the tube.

14. The therapy device of claim 12, further comprising a reduced-pressure source and a dressing, wherein the dressing is fluidly coupled to the reduced-pressure source and the tube.

15. The therapy device of claim 12, further comprising a fill port fluidly coupled to the fluid reservoir and configured to receive fluid.

16. The therapy device of claim 12, further comprising a port fluidly coupling a bottom portion of the fluid reservoir to the tube.

17. The therapy device of claim 12, wherein the therapy device is configured to provide reduced pressure to the tissue site.

* * * * *